US006759064B2

(12) United States Patent
Morré et al.

(10) Patent No.: US 6,759,064 B2
(45) Date of Patent: Jul. 6, 2004

(54) COMPOSITIONS BASED ON VANILLOID-CATECHIN SYNERGIES FOR PREVENTION AND TREATMENT OF CANCER

(75) Inventors: Dorothy M. Morré, West Lafayette, IN (US); D. James Morré, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 10/081,903

(22) Filed: Feb. 22, 2002

(65) Prior Publication Data

US 2003/0072821 A1 Apr. 17, 2003

Related U.S. Application Data

(60) Provisional application No. 60/270,557, filed on Feb. 22, 2001.

(51) Int. Cl.$^7$ .......................... A61K 35/78; A61K 9/22; A61K 31/35; A61K 31/05

(52) U.S. Cl. ..................... 424/729; 424/468; 514/456; 514/732; 514/738

(58) Field of Search ................................ 424/729, 468; 514/456, 732, 738

(56) References Cited

U.S. PATENT DOCUMENTS

| | | |
|---|---|---|
| 4,238,508 A | 12/1980 | Nelson |
| 4,313,958 A | 2/1982 | LaHann |
| 4,401,663 A | 8/1983 | Buckwalter et al. |
| 4,424,205 A | 1/1984 | LaHann et al. |
| 4,443,473 A | 4/1984 | Buckwalter et al. |
| 4,460,602 A | 7/1984 | Buckwalter et al. |
| 4,493,848 A | 1/1985 | LaHann et al. |
| 4,532,139 A | 7/1985 | Janusz et al. |
| 4,544,668 A | 10/1985 | Janusz et al. |
| 4,544,669 A | 10/1985 | LaHann et al. |
| 4,564,633 A | 1/1986 | LaHann et al. |
| 5,354,556 A | 10/1994 | Sparks et al. |
| 5,391,568 A | 2/1995 | Chung |
| 5,461,075 A | 10/1995 | O'Neill et al. |
| 5,569,673 A | 10/1996 | Morré et al. |
| 5,605,810 A | 2/1997 | Morré et al. |
| 5,876,728 A | 3/1999 | Kass et al. |
| 5,989,557 A | 11/1999 | Bombardelli et al. |
| 6,022,718 A | 2/2000 | Iwai et al. |
| 6,063,381 A | 5/2000 | Staggs |
| 6,096,359 A | 8/2000 | Bombardelli et al. |
| 6,201,014 B1 | 3/2001 | Gardiner |

FOREIGN PATENT DOCUMENTS

| | | |
|---|---|---|
| EP | 0089710 | 7/1985 |
| EP | 282127 | 1/1988 |
| GB | 2168974 | 7/1986 |
| GB | 2168975 | 7/1986 |
| GB | 2468976 | 7/1986 |

OTHER PUBLICATIONS

Ahmad et al., 1997, "Green Tea Constituent Epigallocatechin–3–Gallate and Induction of Apoptosis and Cell Cycle Arrest in Human Carcinoma Cells", J. of the Nat. Can. Inst. 89:1881–1886.

Ahmad et al., 1998, "Cancer Chemoprevention by Tea Polyphenols", Nutrition and Chemical Toxicity, John Wiley and Sons, Sussex, England, pp. 301–343.

Ahmad & Mukhtar, 1999, "Green Tea Polyphenols and Cancer: Biologic Mechanisms and Practical Implications", Nutr. Rev. 57:78–83.

Brightman et al., 1992, "A Growth Factor– and Hormone–stimulated NADH oxidase from Rat Liver Plasma Membrane", Biochim. Biophys. Acta 1105: 109–117.

Brown et al., 1969, "Butyramide–utilizing Mutants of *Pseudomonas aeruginosa* 8602 which Produce an Amidase with Altered Substrate Specificity", J. Gen. Microbiol. 1969 57(2):273–85.

Bruno et al., "Stimulation of NADH Oxidase Activity from Rat Liver Plasma Membranes by Growth Factors and Hormones is Decreased or Absent with Hepatoma Plasma Membranes", Biochem. J. 284:625–628.

Caterina & Julius, 2001, "The Vanilloid Receptor: A Molecular Gateway to the Pain Pathway", Annu. Rev. Neurosci. 24:487–517.

Chan et al., 1997, "Inhibition of Inducible Nitric Oxide Synthase Gene Expression and Enzyme Activity by Epigallocatechin Gallate, a Natural Product from Green Tea", Biochem. Pharmacol. 54:1281–1286.

Chen et al., 1996, "Tamoxifen Induces TGF–β1 Activity and Apoptosis of Human MCF–7 Breast Cancer Cells In Vitro", J. Cell. Biochem. 61:9–17.

Chen et al., 1998, "Green Tea Epigallocatechin Gallate Shows a Pronounced Growth Inhibitory Effect on Cancerous Cells But Not on Their Normal Counterparts", Can. Lett. 129:173–179.

(List continued on next page.)

*Primary Examiner*—Christopher R. Tate
(74) *Attorney, Agent, or Firm*—Pennie & Edmonds LLP

(57) ABSTRACT

The invention described herein encompasses methods and compositions of preventing or treating cancer comprising the administration of a combination of catechins and vanilloids. Compositions of catechins include but not limited to, epigallocatechin gallate (EGCg), epicatechin (EC), epicatechin gallate (ECG), epigallocatechin (EGC). In a preferred embodiment the catechins have been treated with tannase. Compositions of vanilloids include, but are not limited to vanillylamine, the head group of capsaicin. The unique compositions of the invention contain various combinations of the catechins and vanilloids, in combination with each other or other therapeutic agents and are used to treat primary and metastatic cancers in humans. The invention also encompasses various modes of administration of the therapeutic compounds, including formulations which may be used as a dietary or nutritional supplement or as a therapeutic compound.

41 Claims, 6 Drawing Sheets

OTHER PUBLICATIONS

Figure 2A:
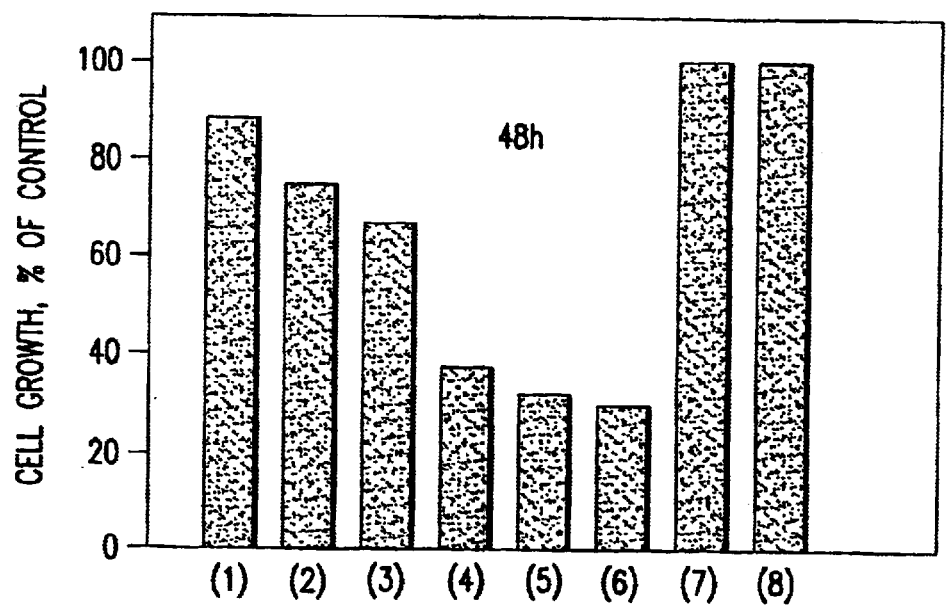

Chueh et al., 1997, "A 33.5–kDa Heat– and Protease–Resistant NADH Oxidase Inhibited by Capsaicin from Sera of Cancer Patients", Arch. Biochem. Biophys. 342:38–44.

Chueh et al., 1997, "The Hormone–responsive NADH Oxidase of the Plant Plasma Membrane Has Properties of a NADH:Protein Disulfide Reductase", J. Biol. Chem. 272:11221.

DeHahn et al., 1997, "NADH Oxidase Activity Present on Both the External and Internal Surfaces of Soybean Plasma Membranes", Biochim. Biophys. Acta 1328:99–108.

Dong et al., 1997, "Inhibition of Tumor Promoter–induced Activator Protein 1 Activation and Cell Transformation by Tea Polyphenols, (–)–Epigallocatechin Gallate, and Theaflavins", Can. Res. 57:4414–4419.

Fujiki et al., 1998, "Cancer Inhibition by Green Tea", Mutation Res. 402:307–310.

Holzer et al., 1979, "Nociceptive Threashold After Neonatal Capsaicin Treatment", Eur. J. Pharm. 58:511–514.

Jancso et al., 1980, "Effect of Capsaicin on Morphine Analgesia—Possible Involvement of Hypothalamic Structures", Naunyn–Schmiedeberg's Arch. Pharmacol., 311:285–288.

Khan et al., "Inhibition of the Skin Tumorigenicity of (±)–7β, 8α–Dihydroxy–9 , 10α–Epoxy–7,8,9,10–Tetrahydrobenzo[a]pyrene by Tannic Acid, Green Tea Polyphenols and Quercetin in Sencar Mice", 1988, Can. Lett. 42:7–12.

Kishi et al., 1999, "The Plasma Membrane NADH Oxidase of HeLa Cells Has Hydroquinone Oxidase Activity", Biochim. Biophys. Acta 1412:66–77.

Liang et al., 1997, "Suppression of Extracellular Signals and Cell Proliferation Through EGF Receptor Binding by (–)–Epigallocatechin Gallate in Human A431 Epidermoid Carcinoma Cells", J. Cell. Biochem. 67:55–65.

Liao et al., 1995, "Growth Inhibition and Regression of Human Prostate and Breast Tumors in Athymic Mice by Tea Epigallocatechin Gallate", Can. Lett. 96:239–243.

Lin & Lin, 1997, "(–)–Epigallocatechin–3–Gallate Blocks the Induction of Nitric Oxide Synthase by Down–regulating Lipopolysaccharide–induced Activity of Transcription Factor Nuclear Factor–kappa b" Mol. Pharmacol. 52:465–472.

Morré, 1994, "Hormone– and Growth Factor–Stimulated NADH Oxidase", J. Bioenerg. Biomemb. 26:421–433.

Morré, 1998, "NADH Oxidase: A Multifunctional Ectoprotein of the Eukaryotic Cell Surface" in Plasma Membrane Redox Systems and their Role in Biological Stress and Disease Kluwer Academic Publishers, Dordrecht, The Netherlands, pp. 121–156.

Morré & Morré, 1995, "Mechanism of Killing of HeLa Cells by the Antitumor Sulfonylurea, N–(4–methylphenylsulfonyl)–N'–(4–chlorophenyl)urea (LY 181984)", Protoplasma 184:188–195.

Morré et al., 1995, "Capsaicin Inhibits Preferentially the NADH Oxidase and Growth of Transformed Cells in Culture", Proc. Natl. Acad. Sci. U.S.A. 92;1831–1835.

Morré et al., 1995, "The Antitumor Sulfonylurea N–(4–methylphenylsulfonyl)–N'–(4–chlorophenyl) urea (LY181984) Inhibits NADH Oxidase Activity of HeLa Plasma Membranes", Biochim. Biophys. Acta 1240:11–17.

Morré et al., 1996, "Capsaicin Inhibits Plasma Membrane NADH Oxidase and Growth of Human and Mouse Melanoma Lines", Eur. J. Can. 32A:1995–2003.

Morré et al., 1997, "Is the Drug–Responsive NADH Oxidase of the Cancer Cell Plasma Membrane a Molecular Target for Adriamycin?" J. Biomemb. Bioenerg. 29:269–280.

Morré & Brightman, 1991, "NADH Oxidase of Plasma Membranes", J. Bioenerg. Biomemb. 23:469–489.

Paschka et al., 1998, "Induction of Apoptosis in Prostate Cancer Cell Lines by the Green Tea Component, (–)–Epigallocatechin–3–Gallate", Can. Lett. 130:1–7.

Piazza et al., 1995, "Antineoplasmic Drugs Sulindac Sulfide and Sulfone Inhibit Cell Growth by Inducing Apoptosis", Can. Res. 55:3110–3116.

Sadzuka et al., 1998, "Modulation of Cancer Chemotherapy by Green Tea", Clin. Can. Res. 4:153–156.

Stoner & Mukhtar, 1995, "Polyphenols as Cancer Chemopreventive Agents", J. Cell. Biochem. 22:169–180.

Suganuma et al., 1999, "Synergistic Effects of (–)–Epigallocatechin Gallate with (–)–Epicatechin, Sulindac, or Tamoxifen on Cancer–preventive Activity in the Human Lung Cancer Cell Line PD–9", Can. Res. 59:44–47.

Sugiyama & Sadzuka, 1998, "Enhancing Effects of Green Tea Components on the Antitumor Activity of Adriamycin Against M5076 Ovarian Sarcoma", Can. Lett. 133:19–26.

Sugunama et al., 1998, "Wide Distribution of [3H](–)–Epigallocatechin Gallate, a Cancer Preventive Tea Polyphenol, in Mouse Tissue", Carcinogenesis 19:1771–1776.

Sugunama et al., 1996, "New Process of Cancer Prevention Mediated through Inhibition of Tumor Necrosis Factor α Expression", Can. Res. 56:3711–3715.

Sun et al., 1987, "NADH Diferric Transferrin Reductase in Liver Plasma Membrane", J. Biol. Chem. 262:15915–15921.

Wang et al., 1989, "Protection Against Polycyclic Aromatic Hydrocarbon–Induced Skin Tumor Initiation in Mice by Green Tea Polyphenols", Carcinogenesis 10:411–415.

Wang et al., 1994, "Inhibitory Effects of Black Tea, Green Tea, Decaffeinated Black Tea, and Decaffeinated Green Tea on Ultraviolet B Light–induced Skin Carcinogenesis in 7,12–Dimethylbenz[a]anthracene–initiated SKH–1 Mice", Cancer Research 54:3428–3435.

Weisburger, 1997, "Tea and Health: A Historical Perspective", Can. Lett. 114:315–317.

Wright et al., 1994, "Inhibition of Apoptosis as a Mechanism of Tumor Promotion", FASEB J 8:654–660.

Yaksh et al., 1979, "Intrathecal Capsaicin Depletes Substance P in the Rat Spinal Cord and Produces Prolonged Thermal Analgesia", Science, 206:481–483.

Yang et al., 1998, "Inhibition of Growth and Induction of Apoptosis in Human Cancer Cell Lines by Tea Polyphenols", Carcinogenesis 19:611–616.

http://www.capsibiol–t.com Capsibiol–T: Green Tea and Capsicum Anticancer Supplement.

http://www.newcancerresearch.com New Cancer Research—Capsibiol–T® Targets and Inhibits the tNOX Protein of Cancer Cells.

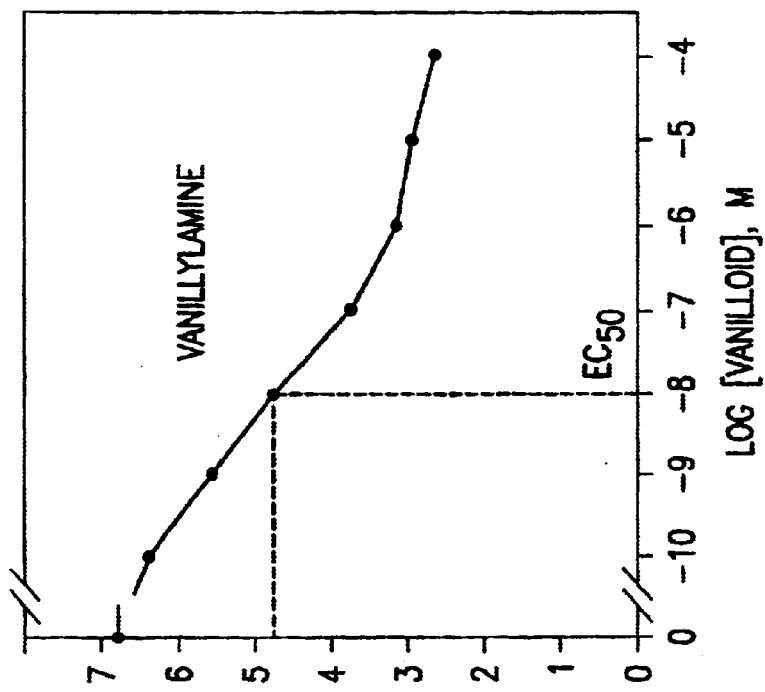
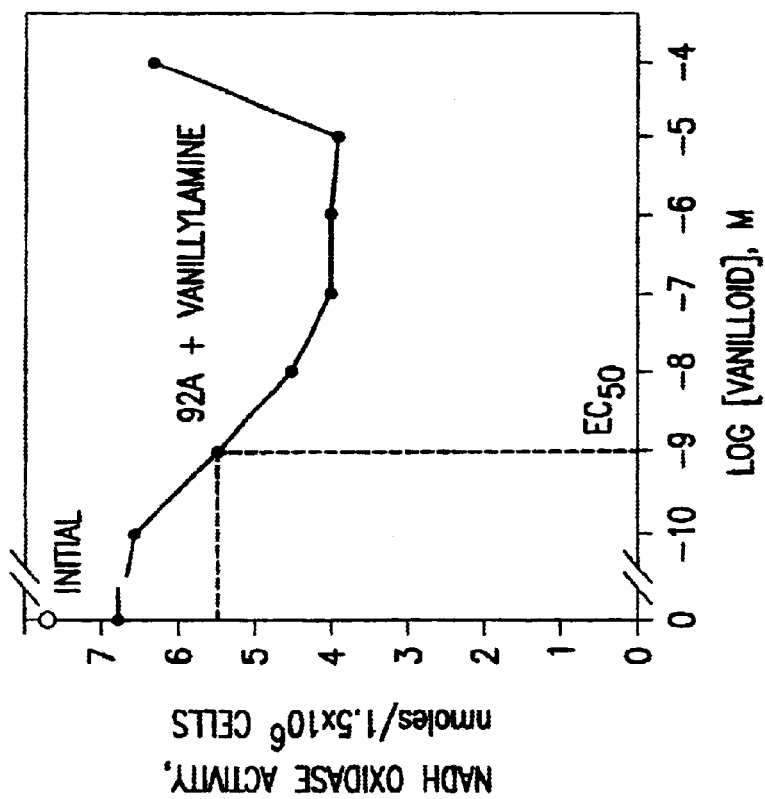

(1): 92A 1:15
(2): 92A 1:15+EGCg 1:1500
(3): 92A 1:15+EGCg 1:1500 + VANILLYLAMINE 1:1500
(4): 92B 1:15
(5): 92B 1:15+EGCg 1:1500
(6): 92B 1:15+EGCg 1:1500 + VANILLYLAMINE 1:1500
(7): EGCg 1:1500
(8): VANILLYLAMINE 1:1500

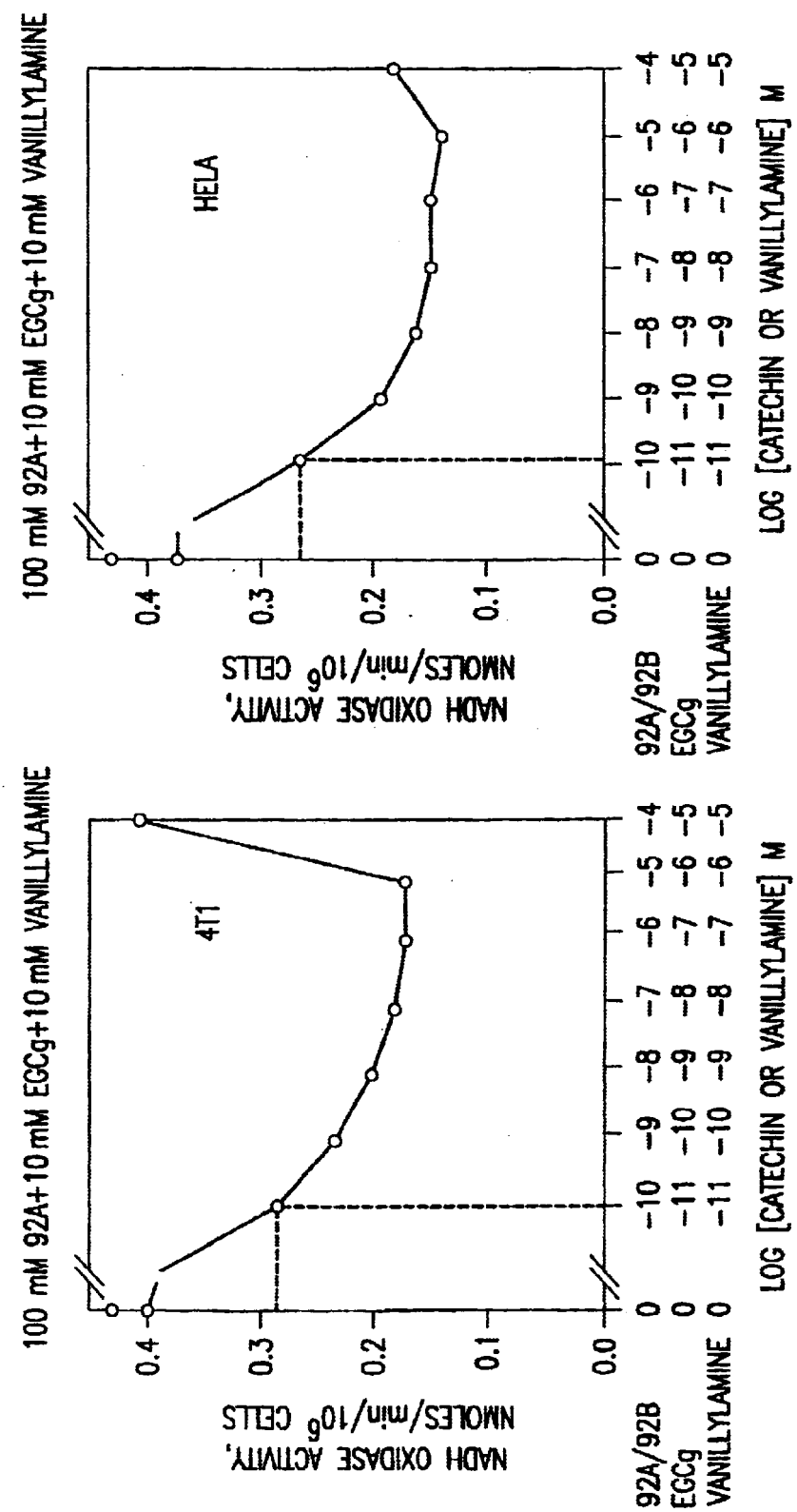

ns which utilize catechins, including but not limited
COMPOSITIONS BASED ON VANILLOID-CATECHIN SYNERGIES FOR PREVENTION AND TREATMENT OF CANCER This application claims benefit of U.S. provisional application serial No. 60/270,557, filed Feb. 22, 2001.

1. INTRODUCTION

The present invention relates to novel methods and compositions which utilize catechins, including but not limited to, epigallocatechin gallate (EGCg), epicatechin (EC), epicatechin gallate (ECG), and epigallocatechin (EGC), which are found in varying levels in tea leaves, in combination with vanilloids, including but not limited to, vanillylamine, the vanilloid head group of capsaicin. The compositions of the invention contain various amounts of the catechins and vanilloids, and optionally, other therapeutic agents. The invention also encompasses the varying modes of administration of the catechins and vanilloids as a dietary or nutritional supplement or as a therapeutic compound.

2. BACKGROUND OF THE INVENTION

2.1. Tea Catechins

Tea is generally in the form of black, oolong, and green tea, all originating from the tea plant, *Camellia sinensis*. Tea is cultivated in approximately thirty countries worldwide, and is consumed globally. Although the level of tea consumption varies around the world, it is believed that tea consumption is second only to water (Ahmad et al., 1998, Nutrition and Chemical Toxicity, John Wiley and Sons, Sussex, England, pp. 301–343). Black tea is consumed predominantly in Western and some Asian countries and green tea is consumed predominantly in China, Japan, India, and a few countries in North Africa and the Middle East (Ahmad et al., 1998, Nutrition and Chemical Toxicity, John Wiley and Sons, Sussex, England, pp. 301–343).

Green tea has been prized as a traditional tonic and has been widely consumed in East Asia. Recent studies have attempted to link green tea to antioxidant benefits including protection against the damage caused by cigarette smoke, pollution, stress, and other toxins (for an overview, see e.g., Mitscher, 1998, The Green Tea Book, Avery Publishing Group, Garden City Park, N.Y. and Weisburger, 1997, Can. Lett. 114:315–317).

An empirical link between green tea and its cancer prevention properties was made in the late 1980s (Khan et al., 1988, Can. Lett. 42:7–12 and Wang et al., 1989, Carcinogenesis 10:411–415). Epidemiological studies show that cancer onset of patients in Japan who had consumed ten cups of green tea per day was 8.7 years later among females and 3 years later among males, compared with patients who had consumed under three cups per day (Fujiki et al., 1998, Mutation Res. 402:307–310). As such, a possible relationship between high consumption of green tea and low incidence of prostate and breast cancer in Asian countries where green tea consumption is high has been postulated (Liao et al., 1995, Can. Lett. 96:239–243 and Stoner and Mukhtar, 1995, J. Cell. Biochem. 22:169–180). However, because of the many variables in lifestyle inherent to such a study, a definitive link between green tea and its cancer prevention effects could not be concluded.

Scientists have now identified many of the natural substances in green tea that may provide the majority of its health benefits. One class of chemicals that has attracted much study is the polyphenols, also known as catechins.

The polyphenols describe a class of substituted phenolic compounds that are known as flavanols or catechins. The polyphenols in green tea that have been identified are catechin (C), epicatechin (EC), gallocatechin (GC), gallocatechin gallate (GCG), epigallocatechin (EGC), epicatechin gallate (ECG), and epigallocatechin gallate (EGCg) (FIG. 1). In addition, caffeine, theobromine, theophylline, and phenolic acids, such as gallic acid, are also present as constituents of green tea in smaller quantities than the polyphenols (Ahmad et al., 1998, Nutrition and Chemical Toxicity, John Wiley and Sons, Sussex, England, pp. 301–343).

Epigallocatechin gallate (EGCg), the major catechin in green tea, has been the focus of many studies to determine if it is responsible for the antioxidant and anti-carcinogenic effects of green tea, as reviewed by Ahmad and Mukhtar, 1999, Nutr. Rev. 57:78–83. The administration of a pharmacologically effective amount of EGCg has been alleged to reduce the incidence of lung cancer in a mammal (U.S. Pat. No. 5,391,568). A bioavailability study showed that frequent green tea consumption results in high levels of EGCg in various body organs, suggesting that green tea consumption may protect against cancers localized to different sites of the body (Sugunama et al., 1998, Carcinogenesis 19:1771–1776).

EGCg has been implicated in blocking DNA transcription of a number of genes in cancer cell lines. For example, in the human epidermal carcinoma cell line A431, EGCg inhibits the DNA and protein synthesis of the growth factor receptors epidermal growth factor receptor (EGF-R), platelet-derived growth factor receptor (PDGF-R), and fibroblast growth factor receptor (FGF-R) (Liang et al., 1997, J. Cell. Biochem. 67:55–65). EGCg has also been implicated in blocking transcription of nitric oxide (NO) synthase by inhibiting the binding of transcription factor NFKB to the NO synthase promotor (Lin and Lin, 1997, Mol. Pharmacol. 52:465–472 and Chan et al., 1997, Biochem. Pharmacol. 54:1281–1286). In the tumor cell line JB6, EGCg inhibits AP-1 transcriptional activity (Dong et al., 1997, Can. Res. 57:4414–4419). These results suggest that EGCg may prevent cancer at the level of gene transcription, i.e., by blocking the DNA synthesis of genes involved in signal transduction pathways.

Further, the focus of many other studies has been the effect of EGCg on apoptosis, or programmed cell death. Apoptosis differs from necrosis, and is regarded as an ideal mechanism for the elimination of cells. Studies have shown that several anti-cancer preventative agents may induce apoptosis, and conversely, several tumor-promoting agents inhibit apoptosis (Wright et al., 1994, FASEB J 8:654–660 and Ahmad and Mukhtar, 1999, Nutr. Rev. 57:78–83).

Much of the prior work in the art has attempted to determine what, if any, effect EGCg has on the growth inhibition and apoptosis induction of cancer cells. A differential growth inhibitory effect was reported in human colorectal cancer cells CaCo-2, breast cancer cells Hs578T, and their non-cancer cell counterparts (Ahmad and Mukhtar, 1999, Nutr. Rev. 57:78–83). EGCg has been implicated in the growth arrest and subsequent induction of apoptosis following cell growth inhibition has been shown in virally transformed fibroblast cells WI138, human epidermal carcinoma cells A431, lung cancer tumor cells H611, prostate cancer cell lines LNCaP, PC-3, and DU145, human carcinoma keratinocytes HaCaT, and mouse lymphoma cells LY-R (Chen et al., 1998, Can. Lett. 129:173–179; Ahmad et al., 1997, J. of the Nat. Can. Inst. 89:1881–1886; Yang et al., 1998, Carcinogenesis 19:611–616; Paschka et al., 1998, Can. Lett. 130:1–7; and Ahmad and Mukhtar, 1999, Nutr.

Rev. 57:78–83). In studies where the apoptotic response was studied in cancer cells versus their non-cancer counterparts, e.g., human carcinoma keratinocytes HaCaT versus normal human epidermal keratinocytes, the apoptotic response to EGCg was reported to be specific to the cancer cells (Ahmad et al., 1997, J. Nat. Can. Inst. 89:1881–1886).

It has been suggested that EGCg induced apoptosis may result from either cell cycle arrest and/or $H_2O_2$ production (Ahmad et al., 1997, J. Nat. Can. Inst. 89:1881–1886; Fujiki et al., 1998, Mutat. Res. 402:307–310; and Yang et al., 1998, Carcinogenesis 19:611–616). EGCg may be involved in the growth regulation of human epidermal carcinoma cells A431 by causing cell cycle arrest of the $G_0$ to $G_1$ phase (Ahmad et al., 1997, J. Nat. Can. Inst. 89:1881–1886). EGCg has also been implicated in phase arrest between $G_2$ to M phase of the cell cycle in human lung cancer cells (Fujiki et al., 1998, Mutat. Res. 402:307–310). In the EGCg induced inhibition of human lung cancer cells, it was suggested that the tumor necrosis factor (TNF) a pathway that is the mode of action of EGCg. Alternatively, the EGCg-induced apoptosis of the lung cancer tumor cells H611 is inhibited by catalase, suggesting the $H_2O_2$ production as a probable cause of apoptosis (Yang et al., 1998, Carcinogenesis 19:611–616).

Despite the above studies, the efficacy of EGCg as a single agent therapy for the prevention of cancer is still unclear. Moreover, the efficacy of EGCg as a therapeutic drug to treat or reverse cancer in a patient is unknown.

Although the focus of much of the prior research has been on EGCg, the putative biological functions of some of the other catechins has been examined. For example, both epicatechin gallate (ECG) and epigallocatechin (EGC) have been reported to be as effective as EGCg in inducing apoptosis of human epidermal carcinoma cells A431 at similar concentrations, whereas epicatechin (EC) did not show a similar effect (Ahmad et al., 1997, J. of the Nat. Can. Inst. 89:1881–1886). Growth inhibition in lung tumor cell lines H661 and H1299 was also observed with EGCg and EGC, whereas ECG and EC were less effective (Yang et al., 1998, Carcinogenesis 19:611–616).

Catechins have been implicated in growth inhibition of the human lung cancer cell line PC-9, with the order of catechin potency being reported as EGCg=ECG>EGC>>>EC (Okabe et al., 1993, Jpn. J. Clin. Oncol. 23:186–190). It has also been demonstrated that catechin combinations of EGCg and EC, ECG and EC, and EGC and EC induce apoptosis of the human lung cancer cell line PC-9 in vitro (Suganuma et al., 1999, Can. Res. 59:44–47). EC is thought to enhance incorporation of EGCg into the cells, which is thought to inhibit TNF a release resulting in the induction of apoptosis (Suganuma et al., 1999, Can. Res. 59:44–47).

Green tea extract, an important source of EGCg, has previously been reported to enhance the effect of the anti-cancer agents, e.g., adriamycin and doxorubicin (Sugiyama and Sadzuka, 1998, Can. Lett. 133:19–26 and Sadzuka et al., 1998, Clin. Can. Res. 4:153–156). Green tea in combination with adriamycin inhibits tumor growth in M5076 ovarian sarcoma cells, whereas adriamycin alone does not inhibit tumor growth in M5076 ovarian sarcoma cells (Sugiyama and Sadzuka, 1998, Can. Lett. 133:19–26). A similar effect is observed with green tea extract and doxorubicin on the same M5076 ovarian sarcoma cell line. Green tea extract, in combination with doxorubicin, also enhances the inhibitory growth effect on Ehrlich ascites carcinoma tumors in tumor-bearing mice, presumably by increasing the concentration of doxorubicin concentration in the tumor, but not in normal tissue (Sadzuka et al., 1998, Clin. Can. Res. 4:153–156).

EGCg has also been shown to enhance the effect of cancer prevention drugs in vitro. For example, EGCg has been shown to enhance the apoptotic effect of sulindac and tamoxifin, presumably by EGCg enhancing the intracellular concentration of the cancer prevention drugs. (Suganuma et al., 1999, Can. Res. 59:44–47). Both sulindac and tamoxifin induce apoptosis of human cancer cells and inhibit TNF α release from BALB/c-3T3 cells (Piazza et al., 1995, Can. Res. 55:3110–3116; Chen et al., 1996, J. Cell. Biochem. 61:9–17; and Sugunamaetal., 1996, Can. Res. 56:3711–3715).

2.2. Vanilloids

Vanilloids are the active ingredients found in Capsicum species, cayenne pepper, black pepper, paprika, cinnamon, clove, mace, mustard, ginger, turmeric, papaya seed and the cactus-like plant *Euphorbia resinifera*. Vanilloid compounds have been generally disclosed to have analgesic, anti-irritant and anti-inflammatory activity. It is believed that vanilloids mediate their biological effects through vanilloid receptors, as reviewed by Caterina & Julius, 2001, Annu. Rev. Neurosci. 24:487–517.

Capsaicinoids are found in extracts of the fruit (peppers) of the Capsicum species, with high amounts being found in the well known chili pepper. The capsaicinoids represent a group of natural products that are vanillylamides of monocarboxylic acids of varying chain lengths from C-8 to C-11 and of varying degrees of unsaturation.

Capsaicin is the most widely studied capsaicinoid. According to World Health Organization statistics, in countries where diets are traditionally high in capsaicin, the cancer death rates for men and women are significantly lower than they are in countries with less chili pepper consumption. When capsaicin was administered to rats receiving carcinogenic agents, the incidence of certain tumors was decreased over controls. As described in U.S. Pat. No. 5,569,673, capsaicin has been found to preferentially inhibit the growth of cancer cells in laboratory studies. As described herein, vanillylamine, the head group of capsaicin, in combination with the green tea polyphenols, was shown to have unexpected potency in the assays and thus potential utility for the prevention and treatment of cancer.

2.3. NADH Oxidase

A unique plasma membrane NADH oxidase (NOX), a unique cell surface protein with hydroquinone (NADH) oxidase and protein disulfide-thiol interchange activities that is responsive to hormone and growth factors has been identified (Brightman et al., 1992, Biochim. Biophys. Acta 1105:109–117; Morré, 1994, J. Bioenerg. Biomemb. 26:421–433; and Morré, 1998, Plasma Membrane Redox Systems and their Role in Biological Stress and Disease, Klewer Academic Publishers, Dordrecht, The Netherlands, pp. 121–156). Further, a hormone-insensitive and drug-responsive form of NOX designated tNOX which is specific to cancer cells has been reported (Bruno et al., 1992, Biochem. J. 284:625–628; Morré and Morré, 1995, Protoplasma 184:188–195; Morré et al., 1995, Proc. Natl. Acad. Sci. U.S.A. 92;1831–1835; Morré et al., 1995, Biochim. Biophys. Acta 1240:11–17; Morré et al., 1996, Eur. J. Can. 32A:1995–2003; and Morré et al., 1997, J. Biomemb. Bioenerg. 29:269–280).

Because the NOX protein is located at the external plasma membrane surface and is not transmembrane, a finctional role as an NADH oxidase is not considered likely (Morré, 1994, J. Bioenerg. Biomemb. 26:421–433; DeHahn et al., 1997, Biochim. Biophys. Acta 1328:99–108; and Morré, 1998, Plasma Membrane Redox Systems and Their Role in Biological Stress and Disease, Klewer Academic Publishers, Dordrecht, The Netherlands, pp. 121–156). While the oxidation of NADH provides a basis for a convenient method to assay the activity, the ultimate electron physiological donor is most probably hydroquinones with specific activities for hydroquinone oxidation greater than or equal to that of NADH oxidation and/or protein thiol-disulfide interchange (Kishi et al., 1999, Biochim. Biophys. Acta 1412:66–77).

CNOX was originally defined as a drug-indifferent constitutive NADH oxidase activity associated with the plasma membrane of non-transformed cells that was the normal counterpart to tNOX (Morré, 1998, Plasma Membrane Redox Systems and Their Role in Biological Stress and Disease, Kiewer Academic Publishers, Dordrecht, The Netherlands, pp. 121–156). Indeed, a 36 kD protein isolated from rat liver and from plants has NOX activity that is unresponsive to tNOX inhibitors (Brightman et al., 1992, Biochim. Biophys. Acta 1105: 109–117).

While cancer cells exhibit both drug-responsive and hormone and growth factor-indifferent (tNOX) as well as drug inhibited and hormone and growth factor dependent (CNOX) activities, non-transformed cells exhibit only the drug indifferent hormone- and drug-responsive CNOX. Among the first descriptions of so-called constitutive or CNOX activity of non-transformed cells and tissues was where the activity of rat liver plasma membranes was stimulated by the growth factor, diferric transferrin (Sun et al., 1987, J. Biol. Chem. 262: 15915–15921). Subsequent work demonstrated that the observed NADH oxidation was catalyzed by a unique enzyme exhibiting responsiveness to several hormones and growth factors (Bruno et al., 1992, Biochem J. 284:625–628). Unlike mitochondrial oxidases, the hormone-stimulated NADH oxidase activity of rat liver plasma membranes is not inhibited by cyanide (Morré, 1994, J. Bioenerg. Biomemb. 26:421–433). The enzyme also was distinguished from other oxidase activities by its response to several common oxidoreductase inhibitors, e.g., catalase, azide and chloroquine, as well as to various detergents e.g., sodium cholate, Triton X-100 and CHAPS (Morre and Brightman, 1991, J. Bioenerg. Biomemb. 23:469–489 and Morré et al., 1997, J. Biomemb. Bioenerg. 29:269–280). Like tNOX of cancer cells, CNOX is a unique membrane-associated protein that is capable of oxidizing NADH but has an activity which is modulated by hormones and growth factors.

2.4. Pathobiology of Cancer

Cancer is characterized primarily by an increase in the number of abnormal cells derived from a given normal tissue, invasion of adjacent tissues by these abnormal cells, and lymphatic or blood-borne spread of malignant cells to regional lymph nodes and to distant sites (metastasis). Clinical data and molecular biologic studies indicate that cancer is a multistep process that begins with minor pre-neoplastic changes, which may under certain conditions progress to neoplasia.

Pre-malignant abnormal cell growth is exemplified by hyperplasia, metaplasia, or most particularly, dysplasia (for review of such abnormal growth conditions, see Robbins and Angell, 1976, Basic Pathology, 2d Ed., W.B. Saunders Co., Philadelphia, pp. 68–79) Hyperplasia is a form of controlled cell proliferation involving an increase in cell number in a tissue or organ, but without significant alteration in structure or function. As but one example, endometrial hyperplasia often precedes endometrial cancer. Metaplasia is a form of controlled cell growth in which one type of adult or fully differentiated cell substitutes for another type of adult cell. Metaplasia can occur in epithelial or connective tissue cells. Atypical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder.

The neoplastic lesion may evolve clonally and develop an increasing capacity for invasion, growth, metastasis, and heterogeneity, especially under conditions in which the neoplastic cells escape the host's immune surveillance (Roitt, Brostoff, and Kale, 1993, Immunology, 3rd ed., Mosby, St. Louis, pp. 17.1–17.12).

There remains a need for treatment of cancer that does not have the adverse effects generally caused by non-selectivity, of conventional chemotherapeutic agents. None of the above studies, which are not to be construed as an admission that any of the above studies is prior art, have suggested the present mechanism by which the catechins are able to differentiate between cancer and non-cancer cells. In contrast, the Inventors have identified a cancer-specific isoform of a unique plasma membrane NADH oxidase (tNOX) which is inhibited by the catechins and the vanilloids, namely capsaicin. Furthermore, the studies cited supra have hypothesized that EGCg mediates its effects intracellularly, since EGCg incorporation into the cell seems to be a prerequisite for the inhibition of TNF α release. Inhibition of tNOX, an extracellular membrane-associated protein by EGCg, and synergistically with other catechins, vanilloids, and anti-cancer agents, results in the selective inhibition of cancer cell growth and ultimately, apoptosis of the cancer cells.

3. SUMMARY OF THE INVENTION

The invention encompasses formulations comprising catechins and vanilloids in ratios that result in synergistic properties. The formulations are used as compositions for the prevention and treatment of cancer or as a dietary or nutritional supplement that protects white blood cells and maintains healthy blood levels. Specific therapeutic regimens, pharmaceutical compositions, and kits are also provided by the invention.

In one embodiment, the invention described herein comprises the administration of catechins in combination with vanilloids, to a mammal as a dietary supplement. In a preferred embodiment, the mammal is a human.

In another embodiment, the invention described herein comprises the administration of a therapeutically effective amount of catechins in combination with vanilloids, to a mammal in need of such therapy. In a preferred embodiment, the mammal is a human. In another embodiment, the invention further encompasses the use of additional therapeutic agent(s) in combination therapy to treat cancer.

In a specific embodiment, the catechins comprise epigallocatechin gallate (EGCg), epicatechin gallate (ECG), epigallocatechin (EGC), epicatechin (EC) or a combination thereof, in combination with one or more vanilloids, such as, but not limited to, vanillylamine. In a preferred embodiment, the ratio of EC to EGCg concentration in the tea catechins is from about 10:1 to about 1000:1. In a preferred embodiment, the catechins have been treated with tannase.

The disclosure is based, in part, on the discovery that catechins, vanilloids, and other anti-cancer therapeutic agents, inhibit the activity of a cancer-specific protein, an isoform of NADH oxidase specific to cancer cells (tNOX). The inhibition of tNOX results in the inhibition of cell growth, and ultimately, apoptosis of the cancer cell, whereas normal cells (which lack tNOX but instead express the isoform CNOX) are less affected. Thus, the invention provides a potent therapeutic effect with reduced or no adverse effects on normal, healthy cells.

Significantly the effect of the catechins such as EGCg is reversible, i.e., if the EGCg is removed, cancer cells resume normal rates of growth. Other discoveries include: (1) EGCg is rapidly cleared from the blood and metabolized, (2) cancer cells must be inhibited from growing for 48 to 72 hours before EGCg-induced apoptosis occurs, and (3) when cancer cells are challenged with $10^{-7}$ M EGCg every two hours during the day, their growth is inhibited, but during the night normal cell growth resumes in the absence of further EGCg addition. Thus, one embodiment of the invention is directed to the administration of sustained release formulations so that a constant level of the catechins is maintained.

Particular compositions of the invention and their uses are described in the sections and subsections which follow.

3.1. Abbreviations

The catechins and target proteins defined herein are abbreviated as follows:

| | |
|---|---|
| (±)-catechin | C |
| (−)-epicatechin | EC |
| gallocatechin | GC |
| gallocatechin gallate | GCG |
| (−)-epigallocatechin | EGC |
| (−)-epicatechin gallate | ECG |
| (−)-epigallocatechin gallate | EGCg |
| nicotinamide adenine dinucleotide | NADH |
| cell surface hydroquinone (NADH) oxidase with protein disulfide-thiol isomerase activity | NOX |
| NOX present in both non-cancer and cancer cells | CNOX |
| NOX specific to cancer cells | tNOX |

4. BRIEF DESCRIPTION OF THE DRAWINGS

FIGS. 1A–1B. Dose response of the NADH oxidase of 4T1 (n=3) cells with 92A (tannase-treated green tea) and synergy with vanillylamine (A) compared to vanillylamine alone (B). The $EC_{50}$ is indicated on each graph.

Figure 2B:
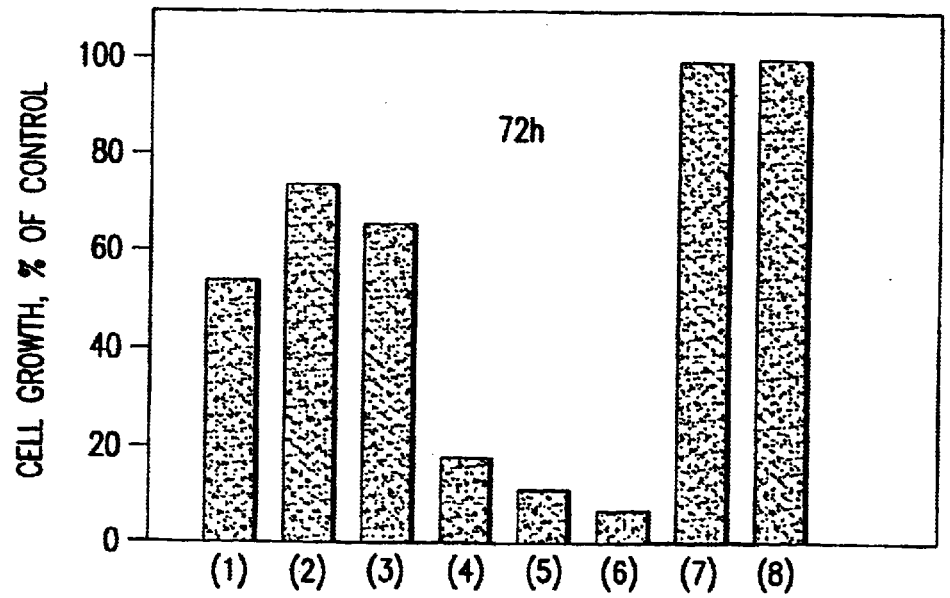
Figures 3A, 3B:
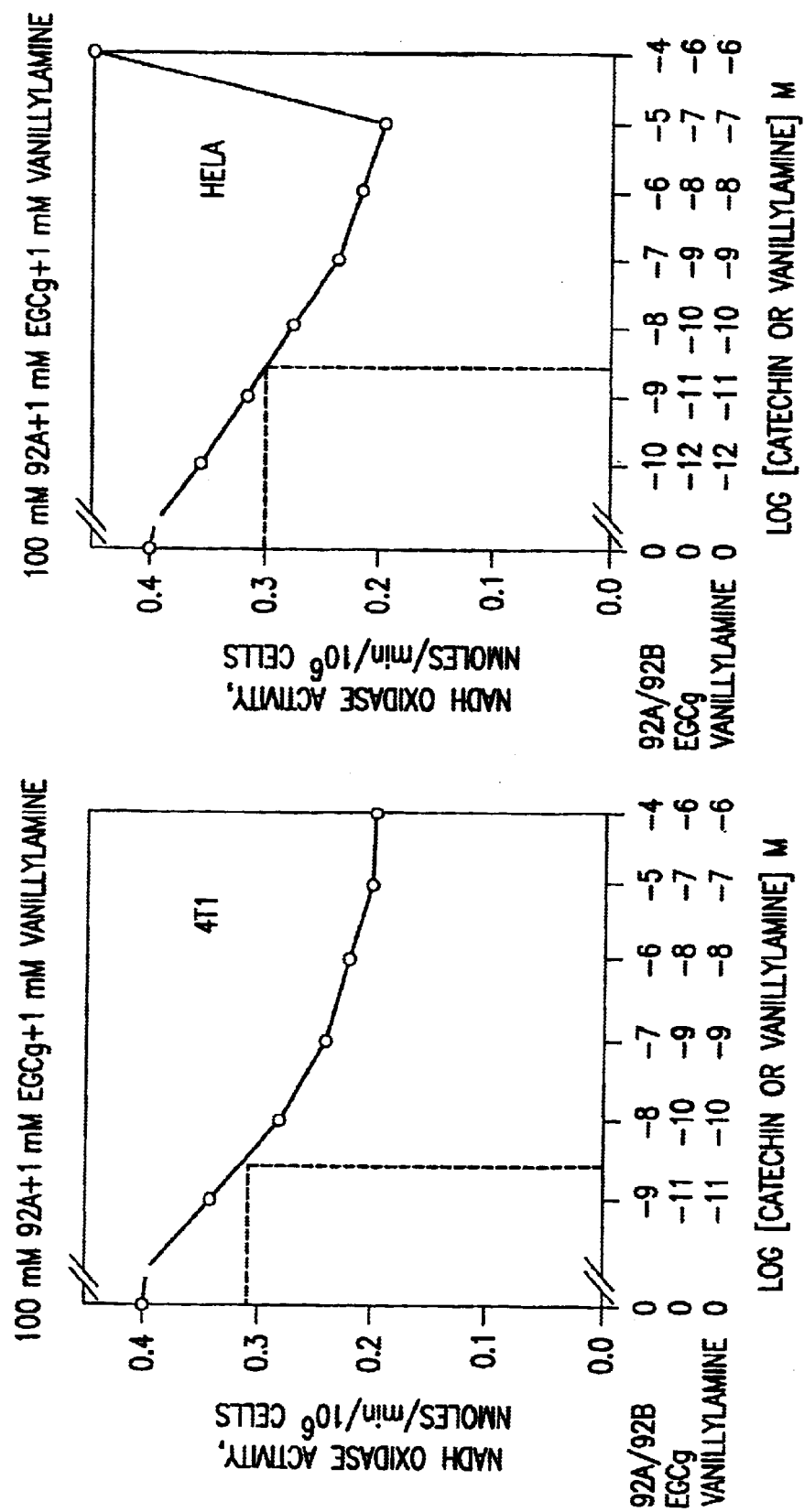
Figures 3C, 3D:
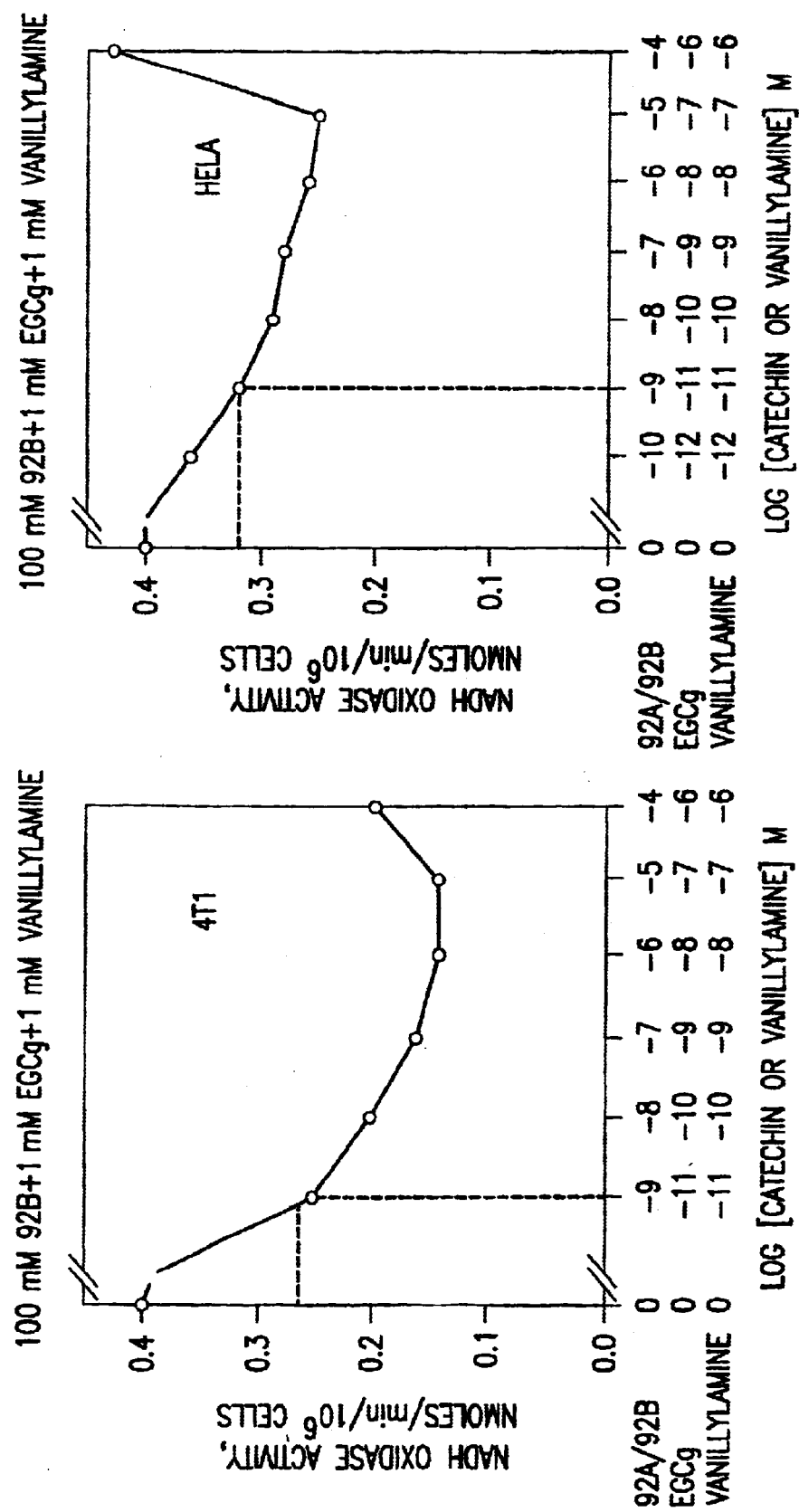
Figures 4C, 4D:
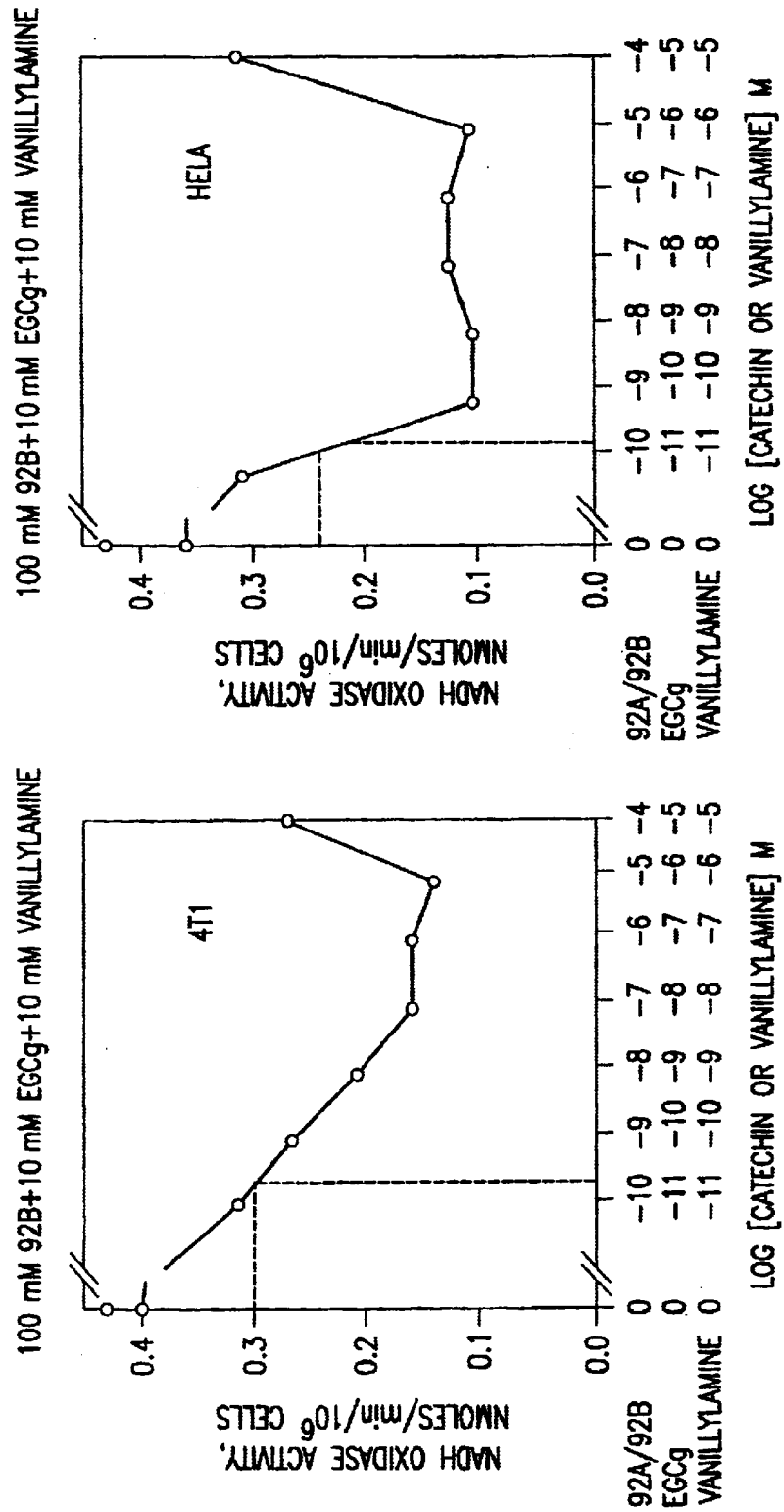

FIGS. 2A–2B. Capitalize synergy of inhibition of HeLa cell growth by a combinati f tannase-treated green tea with (92A) or without 92(B) gallic acid with vanillylamine in a ratio of 100:1:1. The notation 1:15 refers to 100 mM of 92A or 92B diluted in 15 parts of water. The notation 1:1500 refers to the dilution of 100 mM EGCg or vanillylamine in 1500 parts water.

FIGS. 3A–3D. Synergy of inhibition of tNOX activity by tannase treated green tea with (92A) or without (92B) gallic acid with (−)-epigallocatechin gallate (EGCg) plus vanillylamine in a ratio of 100:1:1.

FIGS. 4A–4D. Synergy of inhibition of tNOX activity by a combination of tannase-treated green tea with (92A) or without (92B) gallic acid with vanillylamine in a ratio of 10:1:1.

5. DETAILED DESCRIPTION OF THE INVENTION

The present invention relates to compositions and methods for treatment and prevention of cancer.

The invention is based, in part, on the discovery that vanillylamine, the head group of capsaicin, and catechins, in tea, inhibit the activity of an isoform of NADH oxidase (tNOX) that is specific to cancer cells. A synergy between green tea and vanillylamine was observed in the inhibition of tNOX activity. An unexpected result described herein was the synergy between green tea treated with tannase and vanillylamine. It was believed that the synergistic effect between green tea and vanillylamine was primarily due to an interaction between EGCg and vanillylamine. Thus, the synergy between green tea treated with tannase and vanillylamine was unexpected because there is a significantly reduced level of EGCg in tannase-treated green tea. The inhibition of tNOX results in the inhibition of cell growth, and ultimately, apoptosis of the cancer cell, whereas normal cells, which lack tNOX but express another isoform termed CNOX, are less affected. Accordingly, the invention provides a selective and potent therapeutic effect with reduced or no adverse effects on normal, healthy cells.

In one embodiment, the invention provides a composition comprising tea catechins and vanilloids. In another embodiment, the invention provides a pharmaceutical composition comprising tea catechins, vanilloids and a pharmaceutical carrier. In yet another embodiment, the invention provides a dietary supplement or nutritional composition comprising tea catechins and vanilloids.

One embodiment of the invention described herein pertains to a composition comprising tea catechins and vanilloids. In one embodiment, the composition is a pharmaceutical composition and in another embodiment, the composition is a dietary or nutritional supplement. In a preferred embodiment, the tea catechins contain reduced amounts of EGCg. In this embodiment, the tea catechins have been treated with tannase to reduce the amounts of EGCg.

In a specific embodiment, the catechins comprise epigallocatechin gallate (EGCg), epicatechin gallate (ECG), epigallocatechin (EGC), and epicatechin (EC) or a combination thereof, in combination with one or more vanilloids, such as but not limited vanillylamine.

In one embodiment, the formulation contains about 0.01% of EGCg of the total catechins. In another embodiment, the formulations contain about 0.1% of EGCg of the total catechins. In yet another embodiment, the formulation contains about 1% of EGCg of the total catechins. In yet another embodiment, the formulation contains about 5% of EGCg of the total catechins. In another embodiment, the formulation contain less than 10% of EGCg of the total catechins. In another embodiment, the formulation contain up to 20% of EGCg of the total catechins.

In another embodiment, the ratio of EC to EGCg concentration is about 10:1. In another embodiment, the ratio of EC to EGCg concentration is about 100:1. In yet another embodiment, the ratio of EC to EGCg concentration is about 1000:1.

Further, the concentration of vanilloids is from about 0.01% to 20% of the amount of total catechins. In another embodiment, the formulations contain about 0.1% of vanilloids of the amount of total catechins. In yet another embodiment, the formulations contain about 1% of vanilloids of the amount of total catechins. In yet another embodiment, the formulations contain about 5% of vanilloids of the amount of total catechins. In another embodiment, the formulations contain less than 10% of vanilloids of the amount of total catechins. In another embodiment, the formulations contain up to 20% of vanilloids of the amount of total catechins.

The invention further provides methods for preventing or treating cancer comprising administering compositions comprising tea catechins and vanilloids. In yet another embodiment, the invention encompasses methods for preventing or treating cancer that comprises administering to a subject tea catechins adjunctively with vanilloids such that both catechins and vanilloids are present in vivo and in contact with cancer cells. In various embodiments, the cancer that is prevented or treated by the compositions and methods of the invention is a cancer that comprises cells that express tNOX.

The invention also provides methods for inhibiting the growth and/or proliferation of cancer cells and neoplastic cells comprising contacting the cancer cells and neoplastic cells with a composition comprising both tea catechins and vanilloids. In yet another embodiment, the invention also encompasses methods for inhibiting the growth and/or proliferation of cancer and neoplastic cells comprising contacting the cells with tea catechins and with vanilloids such that when the vanilloids are contacted with the cells, the tea catechins are still providing the anti-cancer activity to the cells, and vice versa the cancer cells and neoplastic cells that are inhibited by the catechin-vanilloid mixtures comprise cells that express tNOX.

Particular compositions of the invention and their uses are described in the sections and subsections which follow.

5.1. Catechin-Vanilloid Formulations
5.1.1. Catechin Formulations

In various embodiments of the invention, tea catechins are used either in the preparation of a composition of the invention that comprises both tea catechins and vanillloids, or in therapeutic or prophylactic methods in which tea catechins are administered adjunctively with vanilloids. Various formulations of tea catechins can be used as above-described. The formulations used in the invention are based on green tea polyphenols, typically found in green tea extracts which comprises 10–15% EGCg, 2–3% ECG, 2% EC, and 2–3% EGC (Suganuma et al., 1999, Can. Res. 59:44–47).

In one embodiment, the present invention provides for a formulation in which EGCg constitutes at least 30% of the total catechins. In a preferred embodiment, EGCg constitutes about 35% to about 45% of the total catechins. In a more preferred embodiment, EGCg constitutes about 40% of the total catechins.

Although the invention encompasses the use of a composition containing certain levels of EGCg alone, it is preferred that EGCg be used in combination with other catechins, more specifically, those described infra.

In another embodiment, the invention provides a formulation in which EGCg constitutes at least 30% of the total catechins and ECG constitutes at least 5% of the total catechins. In a preferred embodiment, EGCg constitutes about 35% to about 45% of the total catechins and ECG constitutes about 10% to about 20% of the total catechins. In a more preferred embodiment, EGCg constitutes about 40% of the total catechins and ECG constitutes about 15% of the total catechins.

In yet another embodiment, the invention provides a formulation in which EGCg constitutes at least 30% of the total catechins and EC constitutes at least 3% of the total catechins. In a preferred embodiment, EGCg constitutes about 35% to about 45% of the total catechins and EC constitutes about 3% to about 15% of the total catechins. In a more preferred embodiment, EGCg constitutes about 40% of the total catechins and EC constitutes about 7% of the total catechins.

In an additional embodiment, the invention provides a formulation in which EGCg constitutes at least 0.01% of the total catechins and EC constitutes an amount which is at least 10 fold greater than the EGCg content of the total catechins. The total catechins may or may not include additional catechins such as ECG, EGC, and C, described above. In a preferred embodiment, EC is present in an amount which is at least 100 fold greater than the EGCg content. In another preferred embodiment, the EC content is at least 1000 fold greater than the EGCg content.

In another embodiment, the amount of EGCg present in the catechin formulation is negligible.

In an additional embodiment, the invention provides a formulation in which EGCg constitutes at least 30% of the total catechins and EGC constitutes at least 1% of the total catechins. In a preferred embodiment, EGCg constitutes about 35% to about 45% of the total catechins and EGC constitutes about 2% to about 5% of the total catechins. In a more preferred embodiment, EGCg constitutes about 40% of the total catechins and EGC constitutes about 3% of the total catechins.

In an additional embodiment, the invention provides a formulation in which EGCg constitutes at least 30% of the total catechins, EC constitutes at least 3% of the total catechins, and ECG constitutes at least 5% of the total catechins. In a preferred embodiment, EGCg constitutes about 35% to about 45% of the total catechins, EC constitutes about 3% to about 15% of the total catechins, and ECG constitutes about 10% to about 20% of the total catechins. In a more preferred embodiment, EGCg constitutes about 40% of the total catechins, EC constitutes about 7% of the total catechins. and ECG constitutes about 15% of the total catechins.

In yet another embodiment, the invention provides a formulation in which EGCg constitutes at least 30% of the total catechins, EC constitutes at least 3% of the total catechins, and EGC constitutes at least 1% of the total catechins. In a preferred embodiment, EGCg constitutes about 35% to about 45% of the total catechins, EC constitutes about 3% to about 15% of the total catechins, and EGC constitutes about 2% to about 5% of the total catechins. In a more preferred embodiment, EGCg constitutes about 40% of the total catechins, EC constitutes about 7% of the total catechins, and EGC constitutes about 3% of the total catechins.

In yet another embodiment, the invention provides a formulation in which EGCg constitutes at least 30% of the total catechins, EC constitutes at least 3% of the total catechins, ECG constitutes at least 5% of the total catechins, and EGC constitutes at least 1% of the total catechins. In a preferred embodiment, EGCg constitutes about 35% to about 45% of the total catechins, EC constitutes about 5% to about 15% of the total catechins, ECG constitutes about 10% to about 20% of the total catechins, and EGC constitutes 2% to about 5% of the total catechins. In a more preferred embodiment, EGCg constitutes about 40% of the total catechins, EC constitutes about 7% of the total catechins. ECG constitutes about 15% of the total catechins, and EGC constitutes about 3% of the total catechins.

In yet another embodiment, the invention provides a formulation in which EGCg constitutes at least 30% of the total catechins, EC constitutes at least 3% of the total catechins, ECG constitutes at least 5% of the total catechins, EGC constitutes at least 1% of the total catechins, and C constitutes at least 5% of the total catechins. In a preferred embodiment, EGCg constitutes about 35% to about 45% of the total catechins, EC constitutes about 5% to about 15% of the total catechins, ECG constitutes about 10% to about 20% of the total catechins, EGC constitutes 2% to about 5% of the total catechins, and C constitutes about 10% to about 20% of the total catechins. In a more preferred embodiment, EGCg constitutes about 40% of the total catechins, EC constitutes about 7% of the total catechins. ECG constitutes about 15% of the total catechins, EGC constitutes about 3% of the total catechins, and C constitutes about 15% of the total catechins.

In one embodiment, the invention provides a formulation which contains about 0.01% of EGCg of the total catechins. In another embodiment, the formulations contain about 0.1% of EGCg of the total catechins. In yet another embodiment, the formulation contains about 1.0% of EGCg of the total catechins. In yet another embodiment, the formulation contain about 5.0% of EGCg of the total catechins. In another embodiment, the formulation contains less than 10% of EGCg of the total catechins.

In another embodiment, the ratio of EC to EGCg concentration is about 10:1. In another embodiment, the ratio of EC to EGCg concentration is about 100:1. In yet another embodiment, the ratio of EC to EGCg concentration is about 1000:1.

In various embodiment, the level of caffeine in the formulation is generally less than about 5% and is preferably less than 0.5% of the polyphenols.

The catechin formulations described above can be made by infusing natural tea (see, e.g., Wang et al., 1994, Cancer Research 54:3428–3435 or U.S. Pat. No. 6,096,359, which is hereby incorporated by reference in its entirety) or by using tea concentrates that are commerically available (e.g., Tegreen™, Pharmanex, Brisbane, Calif.). The concentrations of the individual catechins in a formulation can be manipulated by adding purified catechins, which may be purchased (e.g., from Sigma, St. Louis, Mo.), or alternatively, purified from green tea by methods known to one of skill in the art (e.g., by high pressure liquid chromatography, "HPLC"). Many other methods for making tea-based compositions with altered levels of tea catechins can be used. For example, methods with generating tea formulations with reduced amounts of EGCg are disclosed in U.S. patent application Ser. No. 09/640,768, which is hereby incorporated by reference in its entirety.

5.1.2. Vanilloid Formulations

Vanilloids are the active ingredients found in fruit (peppers) of the Capsicum species and have been generally disclosed to have analgesic, anti-irritant and anti-inflammatory activity. It is believed that vanilloids mediate their biological effects through vanilloid receptors, as reviewed by Caterina & Julius, 2001, Annu. Rev. Neurosci. 24:487–517. Naturally occurring vanilloids are found not only in present in Capsicum extracts, but also from sources such as, but not limited to, cayenne pepper, black pepper, paprika, cinnamon, clove, mace, mustard, ginger, turmeric, papaya seed and *Euphorbia resinifera*. Included in the definition of the naturally occurring vanilloid compounds are both crude extracts (obtained by extracting the natural product) and purified extracts of active vanilloid compounds (obtained either by synthesis or by refining a crude extract).

As used herein, vanilloids include, but are not limited to, the naturally occurring vanilloids described above, capsaicinoids, capsaicins, vanillylamines, vanillyamides, Capsicum extracts, and derivatives thereof. Examples of such vanilloid derivatives include, but are not limited to, amide derivatives, carbamate and urea derivatives, and the like.

The definition of vanilloids also encompass the capsaicinoids, which are found in extracts of the fruit (peppers) of the Capsicum species and represent a group of natural products that are vanillylamides of monocarboxylic acids of varying chain lengths from C-8 to C-11 and of varying degrees of unsaturation. When capsaicin, the most widely studied capsaicinoid, was administered to rats receiving carcinogenic agents, the incidence of certain tumors was decreased over controls. As disclosed in U.S. Pat. No. 5,569,673, which is incorporated by reference in its entirety, capsaicin has been found to preferentially inhibit the growth of cancer cells in laboratory studies. As described in U.S. Pat. No. 4,313,958, which is incorporated by reference in its entirety, capsaicin can be readily obtained by the ethanol extraction of the fruit of *Capsicum frutescens* or *Capsicum annum*. It is available commercially from a variety of suppliers, and can also be prepared synthetically by published methods. The vascular and respiratory side effects of intravenous and intra-arterial capsaicin are well documented (see, e.g., Ton et al., Br. J. Pharmacol., 1955, 10:175–182).

In a preferred embodiment, the vanilloid is the vanillylamine head group of capsaicin. As described herein, vanillylamine was effective in prevention of metastasis in a mouse model and without the neurological discomfort and possible toxicity. The vanillylamine can be purified from capsaicinoids, as described below. Alternatively, the vanillylamine can be purchased from a commercial source, e.g., 4-hydroxy-3-methoxybenzy amine hydrochloride purchased from Aldrich Chemical Company, P.O. Box 385, Milwaukee, Wis. 53201.

The following vanilloid compounds are non-limiting examples described in U.S. Pat. Nos. 5,461,075 and 6,201,014, and references in which they are disclosed; all of the following references are hereby incorporated herein in their entirety by reference. Capsaicins include, but are not limited to: capsaicin (trans-8-methyl-N-vanillyl-6-nonenamide) and "synthetic" capsaicin (N-vanillylnonanamide) in U.S. Pat. No. 4,313,958; synthetic capsaicin in PCT Publication No. WO 96/40079; capsaicin in Yaksh et al., 1979, Science, 206:481–483; capsaicin in Jancso et al., 1980, Naunyn-Schmiedeberg's Arch. Pharmacol., 311:285–288; and capsaicin in Holzer et al., 1979, Eur. J. Pharm. 58:511–514. Related amides include, but are not limited to: N-vanillyl fatty acid amide in U.S. Pat. No. 6,022,718, hydroxyphenylacetamides in European Patent Application 0089710; N-vanillyl sulfonamides in U.S. Pat. No. 4,401,663; hydroxyphenyl-acetamides in U.S. Pat. No. 4,424,205; N-[(substituted phenyl) methyl]-cis-monounsaturated alkenamides in U.S. Pat. No. 4,493,848; N-[(substituted phenyl)methyl]alkynamides in U.S. Pat. No. 4,532,139; methylene substituted N-[(substituted phenyl)methyl] alkanamides in U.S. Pat. No. 4,544,668; N-[(substituted phenyl)methyl]-diunsaturated amides in U.S. Pat. No. 4,544, 669; monoalkenamides in U.S. Pat. No. 4,564,633; N-(substituted alkyl)alkanamides and thioamides in British Patent Specification 2,168,976; and substituted aromatic-araalkanamides in British Patent Specification 2,168,975. Carbamates and ureas include, but are not limited to, N-(3- or 4-hydroxy or 3,4-dihydroxybenzyl) carbamates in U.S. Pat. No. 4,443,473; N-(3-methoxy-4-hydroxybenzyl and phenyl) ureas and thioureas in U.S. Pat. No. 4,460,602; and N-vanillylureas in European Patent Application 0068590.

Other compounds include, but are not limited to, 3-hydroxyacetanilide in U.S. Pat. No. 4,238,508; substituted phenylacetic acid esters in British Patent Specification 2,168,974; beta-aminoethyl-substituted phenyl compounds in European Patent Application No. 282,127; eugenol (2-methoxy-4-(2-propenyl)phenol); zingerone (4-(4-hydroxy-3-methdxyphenyl)-2-butanone); curcumin (1,7-bis (4-hydroxy-3-methoxyphenyl)-1,6-heptadiene-3,5-dione); piperine (1-[5-(1,3-benzodioxol-5-yl)-1-oxo-2,4-pentadienyl]piperidine); and resiniferatoxin (6,7-deepoxy-6, 7-didehydro-5-deoxy-21-dephenyl-21-(phenylmethyl)-20-(4-hydroxy-3-met hoxybenzeneacetate).

The active agents present in Capsicum extracts may be extracted by treatment with bacterial or fungal amidases. These active ingredients are also contemplated as vanilloids of the invention. For example, the extraction of Capsicum may be accomplished by bacterial or fungal enzymes, such as amidases. An example of such an amidase is an amidase isolated from *Pseudomonas aeruginosa*, which is available from Sigma Chemical Co. (St. Louis, Mo.) and disclosed by Brown et al., which is incorporated by reference in its entirety (Brown et al., 1969, J. Gen. Microbiol. 1969 57(2) :273–85). The extraction of the active ingredients of this invention from Capsicum may be accomplished by the following process. The Capsicum peppers are finely ground and reconstituted in water. The mixture is incubated with a bacterial or fungal extract rich in amidases, such as a *Pseudomonas aeruginosa* extract. Alternatively, the amidases may be purified, such as an amidase isolated from *Pseudomonas aeruginosa*, which is available from Sigma Chemical Co. (St. Louis, Mo.). The mixture is incubated for several days, and then neutralized by heating or adding alcohol. It is understood that one or ordinary skill in the art may vary the incubation time based on one's needs and would take into account the enzymatic activity of particular amidase used in the reaction, such as, for example, one of skill may be the activity and instructions available from the manufacture if the amidase is purchased as above. Denatured proteins are removed by centrifugation or filtration 0.22 $\mu$m or 0.45 $\mu$m filters are preferred. The supernatant contains the active ingredients of Capsicum of the present invention.

Hydrolysis of capsaicinoids can also yield active agents. The splitting off of the side acid chain, and its replacement with a hydrogen (H) atom yields the primary amine vanillylamine, or 3-methoxy-4-hydroxybenzylamine from vanillylamide.

5.1.3. Combinations of Catechins and Vanilloids

The invention encompasses administration of the catechin formulations and vanilloid listed in Section 5.1.1 and vanilloid formulations listed in Section 5.1.2 administered in combination. The combination of catechins and vanilloids possess a synergistic effect in the inhibition of tNOX activity and the inhibition of cancer cell growth, as demonstrated in the Example presented in Section 6.

The term "synergistic" as used herein refers to a combination which is more effective than the additive effects of any two or more single agents. A determination of a synergistic interaction between catechins, vanilloids, and optionally, one or more other anti-cancer or therapeutic agents may be based on the results obtained from the NOX assays described in Section 6 infra. The results of these assays are analyzed using Chou and Talalay's combination method and Dose-Effect Analysis with Microcomputers' software in order to obtain a Combination Index (Chou and Talalay, 1984, Adv. Enzyme Regul. 22:27–55 and Chou and Chou, 1987, software and manual, Elsevier Biosoft, Cambridge, UK, pp. 19–64). Combination Index values<1 indicates synergy, values>1 indicate antagonism and values equal to 1 indicate additive effects.

Adjunct administration of the tea catechins and vanilloids of the invention means that the two are administered either as a mixture or sequentially. When administered sequentially, the catechins may be administered before or after the vanilloids, so long as the first administered agent is still providing anti-cancer activity in the animal when the second agent is administered. Any of the modes of administration described infra may be used in combination to deliver the tea catechins and vanilloids.

The present invention is to be understood as embracing all such regimens and the term "adjunct administration" is to be interpreted accordingly. When the tea catechins and vanilloids are administered adjunctively as a mixture, they are preferably given in the form of a composition comprising both agents. Thus, one embodiment of the invention provides for a pharmaceutical composition comprising tea catechins and vanilloids, and optionally, a pharmaceutically acceptable carrier. In another embodiment, when the tea catechins and vanilloids are administered adjunctively as a mixture, they are given in the form of a nutritional or dietary supplement comprising tea catechins and vanilloids.

In one embodiment, a catechin formulation with reduced EGCg, the preparation of which is described in Section 5.1.1 and is disclosed in U.S. patent application Ser. No. 09/640, 768, which is hereby incorporated by reference in its entirety, is used in combination with a vanilloid formulation also described in Section 5.1.2. In a preferred embodiment, the ratio of EC to EGCg is from about 10:1 to about 1000:1. In a preferred embodiment, a catechin formulation with reduced EGCg is used in combination with vanillylamine. In another preferred embodiment, the percentage of EGCg is from about 0.1% to about 20% of the total catechins present in the catechin mixture. In another more preferred embodiment, the percentage of EGCg is from 1% to about 10% of the total catechins. In yet another preferred embodiment, the concentration of vanilloid is from about 0.1% to about 20% as compared to the amount of total catechins present in the catechin mixture. In another preferred embodiment, the concentration of vanilloid is from about 0.1% to about 20% of the amount of total catechins. In yet another preferred embodiment, the vanilloid, such as, but not limited to, vanillylamine is present at about the same concentration as EGCg.

In another embodiment, a catechin formulation, as described in Section 5.1.1 and disclosed in U.S. patent application Ser. No. 09/537,211, which is hereby incorporated by reference in its entirety, which do not reflect the catechin ratios of endogenous green tea, i.e., is non-naturally occurring, is used in combination with a vanilloid formulation described in Section 5.1.2. In a preferred embodiment, a non-naturally occurring catechin formulation is used in combination with vanillylamine.

5.1.4. Combinations of Catechins, Vanilloids, and Other Therapeutic Agents

The methods of the invention also encompasses administrating the catechin formulations described in Section 5.1.1 and vanilloid formulations, or pharmaceutically acceptable salts or derivatives thereof, described in Section 5.1.2 in combination with other therapeutic agents, such as anti-cancer drugs, and optionally, pharmaceutically acceptable carriers. The term "pharmaceutically acceptable carrier" refers to a carrier medium that does not interfere with the effectiveness of the biological activity of the active ingredient, is chemically inert and is not toxic to the patient to whom it is administered. The term "pharmaceutically acceptable salts" refers to salts prepared from pharmaceutically acceptable non-toxic acids and bases, including inorganic and organic acids and bases. As used herein the term "pharmaceutically acceptable derivative" refers to any homolog, analog, or fragment corresponding to the formulations as described in Section 5.1 which exhibits anti-cancer activity and is non-toxic to the subject. The term "therapeutic agent" or "anti-cancer agent" refers to any molecule, compound or treatment that assists in the treatment of a cancer or the diseases caused thereby.

The therapeutic agents include, but are not limited to adriamycin and adriamycin conjugates, mechlorethamine, cyclophosphamide, ifosfamide, melphalan, chlorambucil, hexamethylmelamine, thiotepa, busulfan, carmustine, lomustine, semustine, streptozocin, dacarbazine, methotrexate, fluorouacil, floxuridie, cytarabine, mercaptopurine, thioguanine, pentostatin, vinblastine, vincristine, etoposide, teniposide, actinomycin D, daunorubicin, doxorubicin, bleomycin, plicamycin, mitomycin, L-asparaginase, interferon-alpha, cisplatin, carboplatin, mitoxantrone, hydroxyurea, procarbazine, mitotane, aminoglutethimide, prednisone, hydroxyprogesterone caproate, medroxyprogesterone acetate, megestrol acetate, diethylstilbestrol, ethinyl estradiol, tamoxifen, testosterone propionate, fluoxymesterone, flutamide, leuprolide, acetogenins, e.g., bullatacin, and quassanoids, e.g. simalikalactone D and glaucarubolone, and pharmaceutically acceptable derivatives thereof. The therapeutic agents which have been shown to inhibit tNOX and cancer cell growth include adriamycin, bullatacin, simalikalactone D, and glaucarubolone, descriptions of which are provided in U.S. Pat. No. 5,605,810, which is incorporated by reference in its entirety for all purposes.

Methods of the invention also encompasses administering the catechin formulations-and vanilloid formulations, to cancer patients undergoing chemotherapy and/or irradiation for a primary cancer. In a preferred embodiment, use of the catechin formulations, anti-cancer agents, and combinations thereof provides a method for treating the metastasized, i.e. secondary cancer, in said patients. in said patients.

In another embodiment, the catechin and vanilloid formulations of the invention can be administered with a monoclonal antibody directed against tNOX for the treatment or prevention of cancer. An example of such a monoclonal antibody to the human tNOX protein has been described and has been used in the expression cloning of tNOX from HeLa cells (Chueh et al., 1997, Arch. Biochem. Biophys. 342:38–44).

5.2. Sustained Release Formulation

The invention further provides tea catechins and/or vanilloids that are formulated as sustained release compositions. As used herein, the term "sustained release formulation" refers to any composition that provides slow, controlled, and/or timed release of one or more active ingredients. In one embodiment, the catechins are formulated as a sustained release formulation and are adjunctively administered with the vanilloids. In another embodiment, the vanilloids are formulated as a sustained release formulation and are adjunctively administered with the catechins. In yet another embodiment, both catechins and vanilloids are formulated as sustained release formulations or as a single sustained release formulation.

In a specific embodiment, the sustained release composition of the invention, when administered to a human, results in circulating levels of the catechins, vanilloids, or both at about $10^{-9}$ and $10^{-4}$ M for at least 48 hours. For the prevention of cancer, the circulating levels of the catechins, vanilloids. or both are preferably maintained at up to $10^{-7}$ M for at least 48 hours in the sera. the treatment of cancer, the circulating levels of the catechins, vanilloids, or both are preferably maintained at up to $10^{-5}$ M for at least 48 hours in the sera. The levels are either circulating in the patient systemically, or in a preferred embodiment, localized to the tumor, and in a most preferred embodiment, localized to the cell surface of the cancer cells.

It is understood that the catechin and vanilloid levels are maintained over a certain period of time as is desired and can be easily determined by one of skill in the art using this disclosure and available pharmaceutical compendia. In a preferred embodiment, the invention includes a unique feature of administration comprising a sustained release formulation so a constant level of EGCg is maintained between $10^{-8}$ and $10^{-6}$ M between 48 to 96 hours in the sera.

Such sustained and/or timed release formulations may be made by sustained release means or delivery devices that are well known to those of ordinary skill in the art, such as those described in U.S. Pat. Nos.: 3,845,770, 3,916,899, 3,536,809, 3,598,123, 4,008,719, 4,710,384, 5,674,533, 5,059,595, 5,591,767, 5,120,548, 5,073,543, 5,639,476, 5,354,556, and 5,733,566, the disclosures of which are each incorporated herein by reference. These compositions can be used to provide slow or sustained release of one or more of the active ingredients using, for example, hydropropylmethyl cellulose, other polymer matrices, gels, permeable membranes, osmotic systems, multilayer coatings, microparticles, liposomes, microspheres, or the like, or a combination thereof to provide the desired release profile in varying proportions. Suitable sustained release formulations known to those of ordinary skill in the art, including those described herein, may be readily selected for use with the compositions of the invention. Thus, single unit dosage forms suitable for oral administration, such as, but not limited to, tablets, capsules, gelcaps, caplets, powders, and the like, that are adapted for sustained release are encompassed by the present invention.

In a highly preferred embodiment, the sustained release formulation contains active ingredients such as, but not limited to, microcrystalline cellulose, maltodextrine, ethylcellulose, and magnesium stearate. In yet another highly preferred embodiment, the formulation is synthesized with a CapsuDar® SR (Biodar, Yavne, Israel) microencapsulation which consists of the active ingredients microcrystalline cellulose, maltodextrine, ethylcellulose, and magnesium stearate.

As described above, all known methods for encapsulation which are compatible with the properties of tea catechins and vanilloids are compassed by this invention. The sustained release formulation is encapsulated by coating particles or granules of the composition of the invention with varying thicknesses of slowly soluble polymers or by microencapsulation. In a preferred embodiment, the sustained release formulation is encapsulated with a coating material of varying thickness (e g., about 1 micron to 200 microns) that allows the dissolution of the pharmaceutical composition about 48 hours to about 72 hours after administration to a mammal. In another embodiment, the coating material is a food approved additive. In yet another embodiment, the coating material is sold under the trademark Eudragit RS or RL (Rohm Pharma, Germany).

In another embodiment, the sustained release formulation is a matrix dissolution device, which is prepared by compressing the drug with a slowly soluble polymer carrier into a tablet. In one preferred embodiment, the coated particles have a size range between about 0.1 to about 300 microns, as disclosed in U.S. Pat. Nos. 4,710,384 and 5,354,556, which are incorporated herein by reference in their entireties. Each of the particles is in the form of a micromatrix, with the active ingredient uniformly distributed throughout the polymer.

Sustained release formulations such as those described in U.S. Pat. No. 4,710,384, which is incorporated herein by reference in its entirety, have a relatively high percentage of plasticizer in the coating in order to permit sufficient flexibility to prevent substantial breakage during compression. The specific amount of plasticizer varies depending on the nature of the coating and the particular plasticizer used. The amount may be readily determined empirically by testing the release characteristics of the tablets formed. If the medicament is being released too quickly, then more plasticizer is used. Release characteristics are also a function of the thickness of the coating. When substantial amounts of plasticizer are used, the sustained released capacity of the coating diminishes. Thus, the thickness of the coating may be increased slightly to make up for an increase in the amount of plasticizer. Generally, the plasticizer in such an embodiment will be present in an amount of about 15 to 30 percent of the sustained release material in the coating, preferably 20 to 25 percent and the amount of coating will be from 10 to 25 percent of the weight of active material, preferably 15 to 20 percent. Any conventional pharmaceutically acceptable plasticizer may be incorporated into the coating.

The disclosure of U.S. patent application Ser. No. 09/637,840, which is directed to the use of sustained release formulations of catechins for the treatment and prevention of cancer, is hereby incorporated by reference in its entirety.

5.3. Target Cancers

Cancers that can be prevented or treated by the methods of the present invention include, but not limited to human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenström's macroglobulinemia, and heavy chain disease.

In a preferred embodiment, the cancer is one where circulating levels of tNOX are present in the sera of patients suffering from said cancer, e.g., rectal carcinoma, colon carcinoma, breast carcinoma, ovarian carcinoma, small cell lung carcinoma, colon carcinoma, chronic lymphocytic carcinoma, hairy cell leukemia, osophogeal carcinoma, prostate carcinoma, breast cancer, myeloma, and lymphoma, see e.g., U.S. Pat. No. 5,605,810, which is incorporated by reference in its entirety.

In a preferred embodiment, the patient already has cancer and is undergoing treatment for said cancer. In a specific embodiment, the patient already has cancer but no metastasis. i.e., secondary cancer. In another specific embodiment, the patient already has cancer plus a metastatic cancer. In another specific embodiment, the patient having a cancer is immunosuppressed by reason of having undergone anticancer therapy (e.g., chemotherapy or radiation) prior to administration of the catechin complexes of the invention. In yet another embodiment, the patient is a post-treatment or post-operative cancer patient.

In another specific embodiment, the cancer is a tumor. In a preferred embodiment, the tumor irisatumor of epithelial tissue, lymphoid tissue, connective tissue, bone, or central nervous system.

5.4. Modes of Administration

5.4.1. Sustained Release Formulation

The catechins and vanilloids of the invention may be formulated as a sustained and/or timed release formulation. The levels of circulating catechin and vanilloid compositions must be maintained above some minimum therapeutic dose to reduce the number of cancer cells or to prevent cancer. In one embodiment, the reduction in the number of cancer cells is a result of cell death or apoptosis. In another embodiment, the reduction in the number of cancer cells is a result of inhibition of cell growth. In yet another embodiment, the reduction in the number of cancer cells is a result of cell growth arrest.

All sustained release products have a common goal of improving drug therapy over that achieved by their non-sustained counterparts. Ideally, the use of an optimally designed sustained release preparation in medical treatment is characterized by a minimum of drug substance being employed to cure or control the condition. Advantages of sustained release formulations may include: (1) extended activity of the composition; (2) reduced dosage frequency; and (3) increased patient compliance. In addition, sustained release formulations can be used to affect the time of onset of action or other characteristics, such as blood levels of the composition, and thus can affect the occurrence of side effects.

The sustained release formulations of the invention are designed to initially release an amount of the therapeutic composition that promptly produces the desired therapeutic effect, and gradually and continually release of other amounts of compositions to maintain this level of therapeutic effect over an extended period of time. In order to maintain this constant level in the body, the therapeutic composition must be released from the dosage form at a rate that will replace the composition being metabolized and excreted from the body.

The sustained release of an active ingredient may be stimulated by various inducers, for example pH, temperature, enzymes, water, or other physiological conditions or compounds. The term "sustained release component" in the context of the present invention is defined herein as a compound or compounds, including, but not limited to, polymers, polymer matrices, gels, permeable membranes, liposomes, microspheres, or the like, or a combination thereof, that facilitates the sustained release of the active ingredient.

5.6.2. Modes of Administration of Water-soluble Compositions

If the composition is water-soluble, then it may be formulated in an appropriate buffer, for example, phosphate buffered saline or other physiologically compatible solutions. Alternatively, if the resulting composition has poor solubility in aqueous solvents, then it may be formulated with a non-ionic surfactant such as Tween, or polyethylene glycol. Thus, the compounds and their physiologically acceptable solvates may be formulated for administration by inhalation or insufflation (either through the mouth or the nose) or oral, buccal, parenteral, rectal administration or, in the case of tumors, directly injected into a solid tumor.

5.6.3. Oral Administration

For oral administration, the composition may be in liquid form, (e.g., solutions, syrups or suspensions), or may be presented as a drug product (e.g., capsule or powder) for reconstitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The compositions may take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well-known in the art. In a preferred embodiment, the composition may take the form of a capsule or powder to be dissolved in a liquid for oral consumption.

Preparations for oral administration may be suitably formulated to give controlled release of the active compound. In a preferred embodiment, the compounds of the present invention are formulated as controlled release powders of discrete micro-particles which can be readily formulated in liquid form. The sustained release powder comprises particles containing an active ingredient and optionally, an excipient with at least one non-toxic polymer.

The powder can be dispersed or suspended in a liquid vehicle and will maintain its sustained release characteristics for a useful period of time. These dispersions or suspensions have both chemical stability and stability in terms of dissolution rate. The powder may contain an excipient comprising a polymer, which may be soluble, insoluble, permeable, impermeable, or biodegradable. The polymers may be polymers or copolymers. The polymer may be a natural or synthetic polymer. Natural polymers include polypeptides (e.g., zein), polysaccharides (e.g., cellulose), and alginic acid. Representative synthetic polymers include those described, but not limited to, those described in column 3, lines 33–45 of U.S. Pat. No. 5,354,556 which is incorporated by reference in its entirety. Particularly suitable polymers include those described, but not limited to, those described in column 3, line 46-column 4, line 8 of U.S. Pat. No. 5,354,556 which is incorporated by reference in its entirety.

5.6.4. Buccal Administration

For buccal administration, the compositions may take the form of tablets or lozenges formulated in conventional manner.

5.6.5. Parenteral Administration

The compositions of the invention may be formulated for parenteral administration, e.g., by intramuscular injections or implants for subcutaneous tissues and various body cavities and transdermal devices.

Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

In a preferred embodiment, intramuscular injections are formulated as aqueous or oil suspensions. In an aqueous suspension, the sustained release effect is due to, in part, a reduction in solubility of the active compound upon complexation or a decrease in dissolution rate. A similar approach is taken with oil solutions and suspensions, wherein the release rate of an active compound is determined by partitioning of the active compound out of the oil into the surrounding aqueous medium. Only active compounds which are oil soluble and have the desired partition characteristics are suitable. Oils that may be used for intramuscular injection include, but are not limited to, sesame, olive, arachnis, maize, almond, cottonseed, and castor oil.

A highly developed form of drug delivery that imparts sustained release over periods of time ranging from days to years is to implant a drug-bearing polymeric device subcutaneously or in various body cavities. The polymer material used in an implant, which must be biocompatible and nontoxic, include but are not limited to hydrogels, silicones, polyethylenes, ethylene-vinyl acetate copolymers, or biodegradable polymers.

5.6.6. Rectal Administration

The compositions may also be formulated in rectal compositions such as suppositories or retention enemas, e.g, containing conventional suppository bases such as cocoa butter or other glycerides.

5.6.7. Packs and Kits

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

The invention also provides kits for carrying out the therapeutic regimens of the invention. Such kits comprise in one or more containers having therapeutically or prophylactically effective amounts of the catechin and vanilloid compositions in pharmaceutically acceptable form. The catechin and vanilloid composition in a vial of a kit of the invention may be in the form of a pharmaceutically acceptable solution, e.g., in combination with sterile saline, dextrose solution, or buffered solution, or other pharmaceutically acceptable sterile fluid. Alternatively, the composition may be lyophilized or desiccated; in this instance, the kit optionally further comprises in a container a pharmaceutically acceptable solution (e.g., saline, dextrose solution, etc.), preferably sterile, to reconstitute the complex to form a solution for injection purposes.

In another embodiment, a kit of the invention further comprises a needle or syringe, preferably packaged in sterile form, for injecting the complex, and/or a packaged alcohol pad. Instructions are optionally included for administration of catechin/vanilloid composition by a clinician or by the patient.

5.7. Dosage
5.7.1. Catechins and Vanilloids as a Dietary or Nutritional Supplement In one embodiment of this invention, a formulation comprising catechins and vanilloids may be used as a dietary or nutritional supplement. In this embodiment, the total daily dose ranges of the active catechins and vanilloids for the conditions described herein are generally from about 10 mg to about 800 mg of catechins and from about 0.1 to 80 mg of vanilloids administered in divided doses administered parenterally or orally. A preferred total daily dose is from about 50 mg to about 400 mg of the active catechins and from about 0.5 to 40 mg of vanilloids.

In another embodiment, a total daily dose of a formulation may be used as a dietary supplement is about 10 mg to about 800 mg of active catechins and from about 0.1 to 80 mg of vanilloids administered twice daily (e.g., in the morning and the evening) at a dose of about 5 mg to about 400 mg and from about 0.05 to 40 mg of vanilloids. The dosage forms and compositions may comprise any of the forms and compositions described supra. In a preferred embodiment, the formulation comprising catechins and vanilloids is a tablet, capsule, gel, or a liquid-soluble powder.

5.7.2. Catechins and Vanilloids as a Therapeutic

In another embodiment of the invention, the magnitude of a therapeutic dose of catechins and vanilloids in the acute or chronic management of cancer will vary with the severity of the condition to be treated and the route of administration. The dose, and dose frequency, will also vary according to the age, body weight, condition and response of the individual patient, and the particular catechin and vanilloid combination used. All combinations described in the specification are encompassed as therapeutic, active catechin and vanilloid mixtures and it is understood that one of skill in the art would be able to determine a proper dosage of particular catechin and vanilloid mixtures using the parameters provided in the invention. Furthermore, one of ordinary skill in the art would be able to vary the dose of the vanilloids relative to the amounts of catechins present, based on the guidance provided throughout the invention, particularly as described in Example 6.

In general, the total daily dose ranges of the active catechins for the conditions described herein are generally from about 10 mg to about 1000 mg and from about 0.1 to 100 mg of vanilloids administered in divided doses administered parenterally or orally or topically. A preferred total daily dose is from about 200 mg to about 600 mg of the active catechins and from about 2 to 60 mg of vanilloids.

For example, in one embodiment, the daily dose ranges of catechins for the conditions described herein are generally from about 10 to about 100 mg per kg weight and from about 0.1 to 10 mg of vanilloids. Preferably the catechin and vanilloid formulation of the invention is given daily until remission, followed by two to ten additional cycles, each lasting about 60 days in duration. When the dose is administered orally, a sustained release formulation is preferred so that a fairly constant level of catechins is provided over the course of treatment, which is generally at least 48 hours and preferably at least 96 hours per cycle. As the catechins and vanilloids are not particularly toxic, the formulation may be administered for as long as necessary to achieve the desired therapeutic effect.

In the case where an intravenous injection or infusion composition is employed, a suitable dosage range for use is, e.g., from 1 to about 10 mg per kg body weight of catechins and from about 0.01 to 1 mg per kg body weight of vanilloids total daily.

For treatment of solid tumors, a preferred dosing regimen involves intravenous infusion of about 1 to about 10 mg per kg body weight of catechins and from about 0.01 to 1 mg per kg body weight of vanilloids extract. This daily treatment protocol is repeated once per month until the tumor growth tumor is inhibited or when the tumor shows signs of regression.

In an alternative embodiment of the invention, the effect of the therapy with catechins and vanilloids on cancer treatment can be monitored by any methods known in the art, including but not limited to monitoring circulating tNOX activity in patient sera, as well as more traditional approaches such as determining levels of tumor specific antigens and putative biomarkers, e.g., carcinoembryonic antigens (CEA), alpha-fetoprotein; and changes in morphology and/or size using computed tomographic scan and/or sonogram.

Desirable blood levels may be maintained by a continuous infusion of catechins and vanilloids as ascertained by plasma levels. It should be noted that the attending physician would also know how to and when to adjust treatment to higher levels if the clinical response is not adequate (precluding toxic side effects, if any).

Again, any suitable route of administration may be employed for providing the patient with an effective dosage of the catechin and vanilloid combination of this invention. Dosage forms include tablets, troches, cachet, dispersions, suspensions, solutions, capsules, gel caps, caplets, compressed tablets, sustained release devices, patches, and the like.

The pharmaceutical compositions of the present invention comprise catechins and vanilloids as the active ingredients, as well as pharmaceutically acceptable salts thereof, and may also contain a pharmaceutically acceptable carrier, and optionally, other therapeutic ingredients. The term "pharmaceutically acceptable salts" refers to salts prepared from pharmaceutically acceptable non-toxic acids and bases, including inorganic and organic acids and bases.

The pharmaceutical compositions include compositions suitable for oral and parenteral (including subcutaneous, intramuscular, intrathecal, intravenous, and other injectables) routes, although the most suitable route in any given case will depend on the nature and severity of the condition being treated.

In addition, the catechin and vanilloid carrier could be delivered via charged and uncharged matrices used as drug delivery devices such as cellulose acetate membranes, also through targeted delivery systems such as fusogenic liposomes attached to antibodies or specific antigens.

In practical use, catechins and vanilloids can be combined as the active ingredient(s) in intimate admixture with a pharmaceutical carrier according to conventional pharmaceutical compounding techniques. The carrier may take a wide variety of forms depending on the form of preparation desired for administration, e.g., oral or parenteral (including tablets, capsules, powders, intravenous injections or infusions). In preparing the compositions for oral dosage form any of the usual pharmaceutical media may be employed, e.g., water, glycols, oils, alcohols, flavoring agents, preservatives, coloring agents, and the like; in the case of oral liquid preparations, e.g., suspensions, solutions, elixirs, liposomes and aerosols; starches, sugars, microcrystalline cellulose, diluents, granulating agents, lubricants, binders, disintegrating agents, and the like in the case of oral solid preparations e.g, powders, capsules, and tablets. In preparing the compositions for parenteral dosage form, such as intravenous injection or infusion, similar pharmaceutical media may be employed, e.g., water, glycols, oils, buffers, sugar, preservatives and the like know to those skilled in the art. Examples of such parenteral compositions include, but are not limited to Dextrose 5% (w/v), normal saline or other solutions. The total dose of the catechins and vanilloids may be administered in a vial of intravenous fluid, e.g., ranging from about 0.01 to about 100 mg per kg body weight of catechins and from about 0.0001 to 1 mg per kg body weight of vanilloids. The volume of dilution fluid will vary according to the total dose administered and over the length of the period of time of administration.

An exemplary course of treatment of a patient with cancer or solid cancer can involve daily administration by intravenous infusion of catechins and vanilloids in an aqueous solution at a daily dose of about 1 to about 10 mg of the catechins and from about 0.01 to 1 mg of vanilloids per kg of body weight of the patient. The course of treatment may be repeated for up to ten times over approximately 10 months with a break of about three to six weeks in between courses. The post-remission course of treatment involves infusion of catechins at a daily dose of about 0.01 to about 1 mg and from about 0.0001 to 0.1 mg of vanilloids per kg of body weight of the patient on a daily or weekdays-only basis for a cumulative total of 25 days.

In another embodiment, the invention encompasses the daily dose ranges of catechins for the conditions described herein are generally from about 0.1 to about 15 mg and from about 0.001 to 1.5 mg of vanilloids per kg body weight administered in divided doses administered orally. Preferably the catechin and vanilloid formulation of the invention is given daily, or until remission, followed by two to ten additional cycles, each lasting about 60 days in duration. When the dose is administered orally, a sustained release formulation is preferred so that a fairly constant level of catechins and vanilloids is provided over the course of treatment, which is generally at least 48 hours and preferably at least 96 hours per cycle. As the catechins and vanilloids are not particularly toxic, the formulation may be administered for as long as necessary to achieve the desired therapeutic effect. In the case where an intravenous injection or infusion composition is employed, a suitable dosage range for use is, e.g., from about 0.01 to about 1.5 mg per kg body weight of catechins and from about 0.0001 to 1.5 mg of vanilloids total daily.

For treatment of solid tumors, a preferred dosing regimen involves intravenous infusion of the active catechins of the invention, as described above, in the amount of about 0.01 to about 10 mg and from about 0.0001 to 1 mg of vanilloids per kg body weight per day. This daily treatment protocol is repeated once per month until the tumor growth tumor is inhibited or when the tumor shows signs of regression.

The effect of the therapy with catechins and vanilloids on cancer treatment can be monitored by methods stated supra. Similarly, pharmaceutical compositions and routes of administration are similar as those described supra.

For the purposes described above, the invention also encompasses methods for monitoring patient response to tea catechins and vanilloids. By monitoring circulating tNOX activity in patient sera, it will be possible to determine therapeutic dosages and to monitor therapeutic benefit from tea catechins and vanilloids. The response of neoplastic cells to the subject compositions may be monitored by assaying the blood or urine of the patient for the NOX activity that is responsive to the catechin and vanilloid compositions, i.e., tNOX. Various assays may be used to monitor activity, such as a NOX assay for neoplasia determination see e.g., U.S. Pat. No. 5,605,810. By following the above monitoring procedures, an effective dosage of the subject compositions may be administered in accordance with the requirement of an individual patient.

6. EXAMPLE

SYNERGISTIC EFFECT OFF CATECHINS AND VANILLOIDS

6.1. Materials and Methods

HeLa (ATCC CCL2) cells were grown in 150 cm$^2$ flasks in Minimal Essential Medium (Gibco), pH 7.4, at 37° C. with 10% bovine calf serum (heat inactivated, plus 50 mg/l gentamicin sulfate (Sigma). A mouse mammary tumor subpopulation line 4T1 arising from a BALB/cfC3H mouse (Miller et al., 1981, Brit. J. Cancer 56:561 and Miller et al., 1990, Invasion Metastasis 10:101) was grown in DME 10, Dulbecco's modified Eagle's medium supplemented with 5% fetal calf serum, 5% newborn calf serum, 1 mM mixed non-essential amino acids, 2 mM L-glutamine, penicillin (100 units/ml), and streptomycin (100 $\mu$g/ml).

Cells were quantitated using a standard cytotoxicity assay (Matthews & Neale, 1987, In Lymphokines and Interferons. A Practical Approach. Clemens, M. J. et al., eds. IRL Press, Oxford, p. 221).

NADH oxidase activity may be monitored and measured by virtue of the decrease in absorbance at 340 nm wavelength. A millimolar extinction coefficient of 6.22 for NADH was used to calculate rates of NADH oxidation. Additional tests are such as those described by Morre, 1994, Bioenerg. Biomemb. 26:421, and Chueh et al., 1997, J. Biol. Chem. 272:11221, which are incorporated by reference in their entireties.

The vanillylamine used was a 4-hydroxy-3-methoxybenzy amine hydrochloride (98%) purchased from Aldrich Chemical Company, P.O. Box 385, Milwaukee, Wis. 53201.

6.2. Results

The effect of combinations of tea catechins (including tannase-treated Tegreen with and without gallic acid and EGCg) and the vanilloid vanillylamine, alone and in combination, was demonstrated on (i) cancer cell growth and (ii) NADH oxidase (tNOX) activity. The ratios of tea catechins and vanillyamine was varied to determine optimum ratios for the inhibition of cancer cell growth and the inhibition of tNOX activity. The effect of the catechins and vanillylamine on cancer cell growth is presented in FIG. 2 and Tables 1, 3, and 4. The effect of the catechins and vanillylamines on tNOX activity is presented in FIGS. 1, 3, and 4 and Table 2. The effect of the catechins and vanillylamine on tumors in mice is presented in Table 5.

A novel observation was an unexpected synergy between tannase-treated Tegreen with gallic acid (92A) and vanillylamine in inhibiting the cell surface NADH oxidase, as shown in FIG. 1 and Table 2. A similar synergistic effect on cancer cell growth (i.e., 4T1 and HeLa cells) was observed between tannase-treated Tegreen with gallic acid (92A) or tannase-treated Tegreen without gallic acid (92B) and vanillylamine, as shown in Table 1. The result was unexpected because it was believed that the synergistic effect between green tea and vanillylamine was primarily due to an interaction between EGCg, the most abundant tea catechin, and vanillylamine. As disclosed previously in U.S. patent application Ser. No. 09/640,768, which is incorporated by reference in its entirety, tannase-treated Tegreen contains neglible amounts of EGCg.

TABLE 1

Synergy among tannase-treated Tegreen with (92A) or without (92B) gallic acid and vanillylamine on growth over 48 h of 4T1 and HeLa cells in a 96-well plate assay.

| | | $A_{580}$, % of no addition | |
|---|---|---|---|
| Treatment | Final concentration | 4T1 | HeLa |
| Boiled water control | — | 137 | 142 |
| 92A | 50 μM | 18 | 136 |
| 92A + vanillylamine | 50 μM + 1 μM | 0.1 | 107 |
| 92B | 50 μM | 4 (94)* | 135 (133)* |
| 92B + vanillylamine | 50 μM + 1 μM | 3 (75)* | 110 (105)* |
| Vanillyamine | 1 μM | 144 | 128 |
| EGCg | 20 μM | 58 | 90 |

*Values in parenthesis are for 10 μM 92B

TABLE 2

Inhibition of NADH oxidase of 4T1 and HeLa cells by polyphenols and polyphenols combined with vanillylamine. Assayed were $1.5 \times 10^6$ cells at $10^{10}$, $10^{-9}$, $10^{-8}$, $10^{-7}$, $10^{-6}$, $10^{-5}$ and $10^{-4}$M as illustrated in FIG. 1.

| | $EC_{50}(M)$ | |
|---|---|---|
| Polyphenol source | 4T1 | HeLa |
| 92A (EC + ECG + EGC)* | $10^{-4}$M (n = 3) | $10^{-4}$M (n = 3) |
| Vanillyamine | $5 \times 10^{-9}$M (n = 2) | $10^{-9}$M (n = 1) |
| 92A + vanillylamine | $2 \times 10^{-9}$M (n = 5) | |

*Tannase-treated green tea

A synergy between tannase-treated Tegreen with gallic acid (92A) or without gallic acid (92B), EGCg, and vanillylamine exists, for the inhibition of tNOX activity. The synergistic effect on inhibiting 4T1 and HeLa cell growth is shown in FIG. 2 and Table 4. The synergistic effect on the inhibition of tNOX is presented in FIGS. 3 and 4 and Table 3. The data suggests that a 10:1:1 or a 100:1:1 ratio of tannase-treated Tegreen with (92A) or without gallic acid (92B): EGCg:vanillylamine is effective for inhibiting 4T1 and HeLa (i.e., cancer) cell growth and tNOX activity. Moreover, the above-mentioned components in the 10:1:1 or the 100:1:1 ratios act synergistically to inhibit both cancer cell growth and tNOX activity. Furthermore, as shown in FIG. 2 and Table 4, the inhibitory effect of the tannase-treated Tegreen:EGCg:vanillylamine mixture is maintained up to 72 hours in culture, which is indicative of the potential of the mixture as a cancer therapeutic.

TABLE 3

Synergy among tannase-treated Tegreen with (92A) or without (92B) gallic acid with vanillylamine and EGCg alone or in combination in varying ratios on inhibition of tNOX activity comparing 4T1 and HeLa cells grown in culture.

| | $EC_{50}(M)$ | |
|---|---|---|
| Polyphenol | 4T1 | HeLa |
| 92A | $10^{-4}$ | $10^{-4}$ |
| 92A + EGCg 100:1 | $10^{-8}$ | $10^{-8}$ |
| 92A + EGCg 10:1 | — | $10^{-8}$ |
| 92A + Vanillyamine 10:1 | $10^{-7}$ | $10^{-7}$ |

TABLE 3-continued

Synergy among tannase-treated Tegreen with (92A) or without (92B) gallic acid with vanillylamine and EGCg alone or in combination in varying ratios on inhibition of tNOX activity comparing 4T1 and HeLa cells grown in culture.

| | $EC_{50}(M)$ | |
|---|---|---|
| Polyphenol | 4T1 | HeLa |
| 92A + EGCg + Vanillylamine 100:1:1 | $5 \times 10^{-8}$ | $2 \times 10^{-9}$ |
| 92A + EGCg + Vanillylamine 10:1:1 | $10^{-10}$ | $10^{-10}$ |
| 92B | $>10^{-5}$ | $>10^{-5}$ |
| 92B + EGCg 100:1 | $10^{-8}$ | — |
| 92B + Vanillylamine 100:1 | $2 \times 10^{-9}$ | — |
| 92B + Vanillylamine 10:1 | $10^{-7}$ | $10^{-7}$ |
| 92B + EGCg + Vanillylamine 100:1:1 | $10^{-9}$ | $10^{-9}$ |
| 92B + EGCg + Vanillylamine 10:1:1 | $5 \times 10^{-10}$ | $2 \times 10^{-10}$ |
| EGCg | $10^{-8}$ | $10^{-7}$ |
| Vanillylamine | $5 \times 10^{-9}$ | $10^{-9}$ |

TABLE 4

Synergy among tannase-treated Tegreen with (92A) or without (92B) gallic acid with vanillylamine and EGCg alone or in combination on growth of Hela cells in culture (96 well plate assay). Dilutions are $100 \times$ the final dilutions in the wells.

| EC + EGC + ECG $\times 10^{-2}$ | | Dilution $\times 10^{-2}$ | | Growth, % of control | |
|---|---|---|---|---|---|
| Source | Dilution | EGCg | Vanillylamine | 48 h | 72 h |
| 92A | 1:20 | None | | 91 | 113 |
| | | 1:2000 | | 105 | 125 |
| | | 1:2000 | + 1:2000 | 125 | 130 |
| | | | 1:200 | 80 | 112 |
| | | 1:200 | + 1:200 | 87 | 117 |
| | 1:15 | None | | 36 | 30 |
| | | 1:1500 | | 35 | 35 |
| | | | 1:1500 | 40 | 35 |
| | | 1:1500 | + 1:1500 | 33 | 16 |
| | | | 1:150 | 56 | 61 |
| | | 1:150 | + 1:150 | 28 | 10 |
| 92B | 1:20 | None | | 57 | 20 |
| | | 1:2000 | | 45 | 65 |
| | | 1:2000 | + 1:2000 | 35 | — |
| | | 1:200 | | 64 | 78 |
| | | 1:200 | + 1:200 | 30 | 7 |
| | 1:15 | None | | 21 | 7 |
| | | 1:1500 | | 30 | 10 |
| | | | 1:1500 | 47 | 39 |
| | | 1:1500 | + 1:1500 | 6 | 1 |
| | | | 1:150 | 23 | 1 |
| | | 1:150 | + 1:150 | 24 | 0.3 |
| None | 1:150 | | | 112 | 97 |
| | | | 1:150 | 130 | 120 |

An initial animal trial with the combination of 92A plus vanillylamine is presented in Table 5. The effect of the 92A, vanillylamine, alone and in combination, on tumor weight and metastases of carcinoma cells in mice is presented in Table 5. Tumor growth and metastatic spread were prevented in three animals with 92A, vanillylamine, and a combination of 92A and vanillylamine. Tumor growth in a single animal treated with 92A plus vanillylamine also was blocked and no metastases were observed.

TABLE 5

Effect of polyphenols alone and in combination with vanillylamine on tumor weight and metastases of 4T1 mouse mammary carcinoma cells in BALBc mice.

| Treatment | Tumor weight | Metastasis |
| --- | --- | --- |
| None (n = 8) | 1.00 ± 0.20 | +++ |
| 92A (n = 3) | 1.26 ± 0.14 | +++ |
| Vanillylamine (n = 10) | 0.50 ± 0.20 | +±− |
| 92A + vanillylamine (n = 3) | 0.38 ± 0.35 | --- |

Cells from monolayer culture were suspended in Hank's buffered salt solution and $1 \times 10^6$ cells were injected into the subscapular region in a volume of 0.1 ml.

Anti-metastatic drugs were administered in the dose/injection indicated intratumoral in 0.1 ml total volume on alternate days beginning after palpable tumor masses were discernible (approximately 7 days post implantation) for a total of 6 injections. Appropriate solvent and sham-injected controls were included. At 15 days post tumor implantations, mice were sacrificed and major organs (e.g., lung, liver, lymph nodes) were examined for evidence of metastases.

In contrast, the polyphenol genestein did not exhibit did exhibit synergy with either vanillylamine or EGCg in the NADH oxidase assay (data not shown). Genestein, when tested on the growth of HeLa cells, inhibited but interactions with 1 μM EGCg were additive at low genestein concentrations (data not shown). At higher genestein concentrations, no interactions were seen. Also additive, rather than synergistic, were interactions of genestein with EC or Tegreen™ (data not shown). For example, genestein at 10 μM inhibited 87%, EGCg at 1 μM inhibited 12%, but the combination inhibited 86%. At 100 μM, genestein is toxic.

The present invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

Various publications are cited herein, the disclosures of which are incorporated by reference in their entireties.

What is claimed is:

1. A method for inhibition or treatment of a cancer in a mammal, said method comprising administering to a mammal a composition comprising tea catechins and vanilloids, in amounts effective to inhibit or treat the cancer, wherein the ratio of EC to EGCg concentration in said tea catechins is from about 10:1 to about 1000:1.

2. A method for inhibition or treatment of a cancer in a mammal, said method comprising administering to a mammal a composition comprising tea catechins adjunctively with a composition comprising vanilloids, wherein the amounts of tea catechins and vanilloids administered are effective to inhibit or treat the cancer, wherein the ratio of EC to EGCg concentration in said tea catechins is from about 10:1 to about 1000:1.

3. The method of claim 1 or 2 wherein the ratio of EC to EGCg concentration is about 100:1.

4. The method of claim 1 or 2 wherein the ratio of EC to EGCg concentration is about 1000:1.

5. The methods of claim 1 or 2 wherein gallic acid has been removed from the composition.

6. The method of claim 1 or 2 wherein the mammal is a human.

7. The method of claim 1 or 2 wherein the cancer is selected from a group comprising rectal carcinoma, colon carcinoma, breast carcinoma, ovarian carcinoma, small cell lung carcinoma, colon carcinoma, chronic lymphocytic carcinoma, hairy cell leukemia, osophogeal carcinoma, prostate carcinoma, breast cancer, myeloma, and lymphoma.

8. The method of claim 1 or 2 wherein the cancer is a tumor and wherein said tumor is a tumor of epithelial tissue, lymphoid tissue, connective tissue, bone, or central nervous system.

9. The method of claim 6 wherein the human is immunosuppressed by reason of having undergone anti-cancer therapy.

10. The method of claim 1 or 2 wherein the cancer is a metastases.

11. The method of claim 1 or 2 wherein the level of tea catechins and vanilloids is maintained at constant levels in the sera for at least 48 hours.

12. The method of claim 1 wherein said composition of tea catechins and vanilloids is a sustained release formulation and comprises at least one component which controls the release of said catechins and/or vanilloids.

13. The method of claim 2 wherein said composition of tea catechins or said composition of vanilloids or both are sustained release formulations and comprises at least one component which controls the release of said catechins and/or vanilloids.

14. A method for treatment of a cancer in a mammal, said method comprising administering to a mammal a composition comprising tea catechins and vanilloids, or pharmaceutically acceptable salts thereof, in combination with an effective amount of at least one other anti-cancer agent, in amounts effective to treat the cancer, wherein the cancer is a type having cancer cells which express tNOX, and wherein the ratio of EC to EGCg concentration in said tea catechins is from about 10:1 to about 1000:1.

15. The method of claim 14 in which said other anti-cancer agent is selected from a group consisting of adriamycin and adriamycin conjugates, mechlorethamine, cyclophosphamide, ifosfamide, melphalan, chlorambucil, hexamethylmelamine, thiotepa, busulfan, carmustine, lomustine, semustine, streptozocin, dacarbazine, methotrexate, fluorouacil, floxuridie, cytarabine, mercaptopurine, thioguanine, pentostatin, vinblastine, vincristine, etoposide, teniposide, actinomycin D, daunorubicin, doxorubicin, bleomycin, plicamycin, mitomycin, L-asparaginase, interferon-alpha, cisplatin, carboplatin, mitoxantrone, hydroxyurea, procarbazine, mitotane, aminoglutethimide, prednisone, hydroxyprogesterone caproate, medroxyprogesterone acetate, megestrol acetate, diethylstilbestrol, ethinyl estradiol, tamoxifen, testosterone propionate, fluoxymesterone, flutamide, leuprolide, acetogenins, e.g., bullatacin, and quassanoids, e.g. simalikalactone D and glaucarubolone, and pharmaceutically acceptable derivatives thereof.

16. The method of claim 1, 2, 10, or 14 in which said administration is made via an implantation device.

17. The method of claim 1, 2, 10, or 14 in which said administration is made with a sustained release formulation.

18. The method of claim 8 in which said administration is made parenterally, orally, or directly into the tumor.

19. The method of claim 1, 2, 10 or 14 wherein said vanilloid is vanillylamine.

20. A dietary or nutritional supplement comprising an effective amount of tea catechins and vanilloids to inhibit and/or treat cancer in a mammal, wherein the ratio of EC to EGCg concentration in said tea catechins is from about 10:1 to about 1000:1.

21. The supplement of claim 20 wherein the ratio of EC to EGCg concentration is about 100:1.

22. The supplement of claim 20 wherein the ratio of EC to EGCg concentration is about 1000:1.

23. The supplement of claim 20 wherein gallic acid has been removed from the composition.

24. The supplement of claim 20 wherein the supplement is a sustained release formulation comprising tea catechins and/or vanilloids and at least one component which controls release of said catechins and/or vanilloids.

25. The supplement of claim 20 wherein the supplement is formulated as an oral preparation comprising tablets or powders.

26. The supplement of claim 20 wherein the supplement is formulated as a sterile preparation.

27. The supplement of claim 20 wherein the supplement is formulated as a parenteral solution.

28. The supplement of claim 20 wherein said vanilloid is vanillylamine.

29. The supplement of claim 20 wherein daily dosage of the catechins is about 10 mg to about 800 mg and daily dosage of the vanilloids is about 0.1 mg to about 80 mg.

30. The supplement of claim 29 wherein daily dosage of the catechins is about 50 mg to about 400 mg and daily dosage of the vanilloids is about 0.05 mg to about 40 mg.

31. A pharmaceutical composition comprising an effective amount of tea catechins and vanilloids to inhibit and/or treat cancer in a mammal, wherein the ratio of EC to EGCg concentration in said tea catechins is from about 10:1 to about 1000:1.

32. The composition of claim 31 wherein the ratio of EC to EGCg concentration is about 100:1.

33. The composition of claim 31 wherein the ratio of EC to EGCg concentration is about 1000:1.

34. The composition of claim 31 wherein gallic acid has been removed from the composition.

35. The composition of claim 31 wherein the composition is a sustained release formulation comprising tea catechins and/or vanilloids and at least one component which controls release of said catechins and/or vanilloids.

36. The composition of claim 31 wherein the composition is formulated as an oral preparation comprising tablets or powders.

37. The composition of claim 31 wherein the composition is formulated as a sterile preparation.

38. The composition of claim 31 wherein the composition is formulated as a parenteral solution.

39. The composition of claim 31 wherein said vanilloids is vanillylamine.

40. The composition of claim 31 wherein daily dosage of the catechins is about 10 mg to about 1000 mg and daily dosage of the vanilloids is about 0.1 mg to about 100 mg.

41. The composition of claim 40 wherein daily dosage of the catechins is about 200 mg to about 600 mg and daily dosage of the vanilloids is about 2 mg to about 60 mg.

* * * * *